(12) United States Patent
Giblin et al.

(10) Patent No.: US 7,759,369 B2
(45) Date of Patent: Jul. 20, 2010

(54) PYRIDINE COMPOUNDS FOR THE TREATMENT OF PROSTAGLANDIN MEDIATED DISEASES

(75) Inventors: Gerard Martin Paul Giblin, Harlow (GB); Adrian Hall, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 185 days.

(21) Appl. No.: 11/766,418

(22) Filed: Jun. 21, 2007

(65) Prior Publication Data
US 2008/0249138 A1 Oct. 9, 2008

Related U.S. Application Data

(63) Continuation of application No. 11/722,402, filed as application No. PCT/EP2005/014061 on Dec. 21, 2005.

(30) Foreign Application Priority Data

| Dec. 23, 2004 | (GB) | ................... | 0428263.8 |
| Apr. 26, 2005 | (GB) | ................... | 0508458.7 |
| Dec. 2, 2005 | (GB) | ................... | 0524675.6 |

(51) Int. Cl.
A61K 31/44 (2006.01)
C07D 213/79 (2006.01)

(52) U.S. Cl. ........................... 514/356; 546/326
(58) Field of Classification Search ............... 568/647; 546/298, 326; 514/354, 356
See application file for complete search history.

(56) References Cited

U.S. PATENT DOCUMENTS

| 5,811,459 A * | 9/1998 | Breault et al. ............ 514/555 |
| 6,362,009 B1 | 3/2002 | Munoz et al. |

FOREIGN PATENT DOCUMENTS

| EP | 0388682 A1 | 3/1990 |
| EP | 0752421 B1 | 7/1996 |
| JP | 2602340 A1 | 7/1976 |
| JP | 2001089452 A | 4/2001 |
| WO | 9517888 A1 | 7/1995 |
| WO | 9603380 A1 | 2/1996 |
| WO | 9606822 A1 | 3/1996 |
| WO | 9611902 A1 | 4/1996 |
| WO | 9618616 A1 | 6/1996 |
| WO | 9700863 A1 | 1/1997 |
| WO | 9700864 A1 | 1/1997 |
| WO | 9941237 A1 | 8/1999 |
| WO | 0049015 A1 | 8/2000 |
| WO | 0119814 A3 | 3/2001 |
| WO | 03084917 A1 | 10/2003 |
| WO | 03101959 A1 | 12/2003 |
| WO | 2004039753 A1 | 5/2004 |
| WO | 2004043392 A2 | 5/2004 |
| WO | 2004083185 A3 | 9/2004 |
| WO | 2005037786 A1 | 4/2005 |
| WO | 2005037793 A1 | 4/2005 |
| WO | 2005037794 A1 | 4/2005 |
| WO | 2005040128 A1 | 5/2005 |
| WO | 2005054191 A1 | 6/2005 |
| WO | 2005108369 A1 | 11/2005 |

OTHER PUBLICATIONS

Y Ducharme, Marc Blouin, Marie-Claude Carriere, Anne Chateauneuf, Bernard Cote, Danielle Denis, Richard Frenette, Gillian Greig, Stacia Kargman, Sonia Lamontagne, Evelyn Martins, Francoise Nantel, Gary O'Neill, Nicole Sawyer, Kathleen M Metters and Richard W Friesen; 2,3-Diarylthiophenes as selective EP1 receptor antagonists; Bioorganic & Medicinal Chemistry Letters; Jan. 7, 2005; 15; 1155-1160; Elsevier.

* cited by examiner

*Primary Examiner*—Janet L Andres
*Assistant Examiner*—Binta M Robinson
(74) *Attorney, Agent, or Firm*—Bonnie L. Deppenbrock

(57) ABSTRACT

Compounds of formula (I) or a pharmaceutically acceptable derivative thereof:

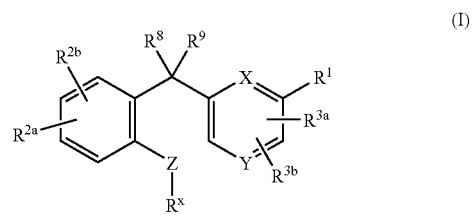

(I)

wherein X, Y, Z, $R^{2a}$, $R^{2b}$, $R^{3a}$, $R^{3b}$, $R^8$, $R^9$, and $R^x$ are as defined in the specification, a process for the preparation of such compounds, pharmaceutical compositions comprising such compounds and the use of such compounds in medicine.

6 Claims, No Drawings

PYRIDINE COMPOUNDS FOR THE TREATMENT OF PROSTAGLANDIN MEDIATED DISEASES

CROSS-REFERENCE TO RELATED APPLICATIONS

This application is filed as a Continuation application of U.S. Ser. No. 11,722,402, filed Jun. 21, 2007, which was a United States National Phase Application of International Patent Application Serial No. PCT/EP2005/014061 filed on Dec. 21, 2005, which claims priority from 0428263.8 filed on Dec. 23, 2004, 0508458.7 filed on Apr. 26, 2005, and 0524675.6 filed on Dec. 2, 2005, each filed in the United Kingdom.

FIELD OF THE INVENTION

This invention relates to pyridine compounds, to processes for their preparation, to pharmaceutical compositions containing them and to their use in medicine, in particular their use in the treatment of conditions mediated by the action of $PGE_2$ at the $EP_1$ receptor.

BACKGROUND OF THE INVENTION

Prostaglandin receptors, including the $EP_{1-4}$, DP, FP IP and TP receptors are the effector proteins for the products (prostaglandins) downstream of COX-1/2 activation ($PGE_2$, PGD2, PGF2a, PGI2 and thromboxane respectively). The NSAIDS (non-steroidal anti-inflammatory drugs) are indiscriminate cyclooxygenase inhibitors and reduce the levels of these prostaglandins. This in turn reduces the action of the prostaglandins at their respective receptors. In view of the relatively large number of receptors affected, the pharmacology of the NSAIDS is complex.

The $EP_1$ receptor is a 7-transmembrane receptor and its natural ligand is the prostaglandin $PGE_2$. $PGE_2$ also has affinity for the other EP receptors (types $EP_2$, $EP_3$ and $EP_4$). The $EP_1$ receptor is associated with smooth muscle contraction, pain (in particular inflammatory, neuropathic and visceral), inflammation, allergic activities, renal regulation and gastric or enteric mucus secretion.

We have now found a novel group of compounds which bind with high affinity to the $EP_1$ receptor. These compounds are antagonists of the $EP_1$ receptor.

A number of review articles describe the characterization and therapeutic relevance of the prostanoid receptors as well as the most commonly used selective agonists and antagonists: *Eicosanoids; From Biotechnology to Therapeutic Applications*, Folco, Samuelsson, Maclouf, and Velo eds, Plenum Press, New York, 1996, chap. 14, 137-154 and *Journal of Lipid Mediators and Cell Signalling*, 1996, 14, 83-87 and *Prostanoid Receptors, Structure, Properties and Function*, S. Narumiya et al, Physiological Reviews 1999, 79(4), 1193-126. An article from *The British Journal of Pharmacology*, 1994, 112, 735-740 suggests that Prostaglandin $E_2$ ($PGE_2$) exerts allodynia through the $EP_1$ receptor subtype and hyperalgesia through $EP_2$ and $EP_3$ receptors in the mouse spinal cord. Furthermore an article from *The Journal of Clinical Investigation*, 2001, 107 (3), 325 shows that in the $EP_1$ knockout mouse pain-sensitivity responses are reduced by approximately 50%. Two papers from *Anesthesia and Analgesia* have shown that (2001, 93, 1012-7) an $EP_1$ receptor antagonist (ONO-8711) reduces hyperalgesia and allodynia in a rat model of chronic constriction injury, and that (2001, 92, 233-238) the same antagonist inhibits mechanical hyperalgesia in a rodent model of post-operative pain. S. Sarkar et al in *Gastroenterology*, 2003, 124(1), 18-25 demonstrate the efficacy of $EP_1$ receptor antagonists in the treatment of visceral pain in a human model of hypersensitivity. In The American Physiological Society (1994, 267, R289-R-294), studies suggest that $PGE_2$-induced hyperthermia in the rat is mediated predominantly through the $EP_1$ receptor.

The TP (also known as $TxA_2$) receptor is a prostanoid receptor subtype stimulated by the endogenous mediator thromboxane. Activation of this receptor results in various physiological actions primarily incurred by its platelet aggregatory and smooth muscle constricting effects, thus opposing those of prostacyclin receptor activation.

TP receptors have been identified in human kidneys (G. P. Brown et al, *Prostaglandins and other lipid mediators*, 1999, 57, 179-188) in the glomerulus and extraglomerular vascular tissue. Activation of TP receptors constricts glomerular capillaries and suppresses glomerular filtration rates (M. D. Breyer et al, *Current Opinion in Nephrology and Hypertension*, 2000, 9, 23-29), indicating that TP receptor antagonists could be useful for renal dysfunction in glomerulonephritis, diabetes mellitus and sepsis.

Activation of TP receptors induces bronchoconstriction, increase in microvascular permeability, formation of mucosal oedema and mucus secretion, typical characteristic features of bronchial asthma (T. Obata et al, *Clinical Review of Allergy*, 1994, 12(1), 79-93). TP antagonists have been investigated as potential asthma treatments resulting in, for example, orally active Seratrodast (AA-2414) (S. Terao et al, *Yakugaku Zasshi*, 1999, 119(5), 377-390). Ramatroban is another TP receptor antagonist currently undergoing phase III clinical trials as an anti-asthmatic compound.

Antagonists at the TP receptor have been shown to have a gastroprotective effect. In rats it has been shown that SQ 33961 and BM 13505 inhibit gastric lesions induced by taurocholate acid, aspirin or indomethacin (E. H. Ogletree et al, *Journal of Pharmacology and Experimental Therapeutics*, 1992, 263(1), 374-380.

Certain compounds of the present invention also exhibit antagonism at the TP receptor and are therefore indicated to be useful in treating conditions mediated by the action of thromboxane at the TP receptor. Such conditions include those disclosed in WO 2004/039807 (Merck Frosst Canada & Co) which is incorporated herein by reference, and include respiratory diseases e.g. asthma, allergic diseases, male erectile dysfunction, thrombosis, renal disorders and gastric lesions.

WO 96/06822 (7 Mar. 1996), WO 96/11902 (25 Apr. 1996), EP 752421-A1 (8 Jan. 1997), WO 01/19814 (22 Mar. 2001), WO 03/084917 (16 Oct. 2003), WO 03/101959 (11 Dec. 2003), WO 2004/039753 (13 May 2004), WO 2004/083185 (30 Sep. 2004), WO 2005/037786 (28 Apr. 2005), WO 2005/037793 (28 Apr. 2005), WO 2005/037794 (28 Apr. 2005), WO 2005/040128 (6 May 2005), WO 2005/054191 (16 Jun. 2005) and WO2005/108369 (17 Nov. 2005) disclose compounds as being useful in the treatment of prostaglandin mediated diseases.

P. Lacombe et al (220th National Meeting of The American Chemical Society, Washington D.C., USA, 20-24 Aug., 2000) disclosed 2,3-diarylthiophenes as ligands for the human $EP_1$ prostanoid receptor. Y. Ducharme et al (18th International Symposium on Medicinal Chemistry; Copenhagen, Denmark and Malmo, Sweden; 15th-19th Aug. 2004) disclosed 2,3-diarylthiophenes as $EP_1$ receptor antagonists. Y. Ducharme et al, *Biorg. Med. Chem. Lett.*, 2005, 15(4): 1155 also discloses 2,3-diarylthiophenes as selective $EP_1$ receptor antagonists.

DT 2602340 A1 discloses certain benzyl picolinic acid derivatives as hypotensive agents and dopamine β-hydroxylase inhibitors.

DESCRIPTION OF THE INVENTION

Accordingly the present invention provides compounds of formula (I):

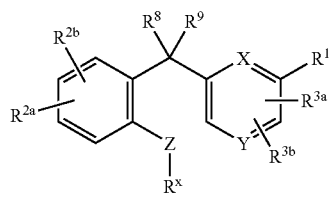

wherein:

X is N and Y is CH, or X is CH and Y is N;

Z is O, S, SO or $SO_2$;

$R^1$ is $CO_2H$, $CONHSO_2R^6$, $CH_2CO_2H$, $NR^4COR^7$, tetrazole or $CH_2$tetrazole;

$R^{2a}$ and $R^{2b}$ are each independently selected from hydrogen, halo, CN, $SO_2$alkyl, $SR^5NO_2$, optionally substituted alkyl, optionally substituted alkoxy, optionally substituted aryl, and optionally substituted heteroaryl;

$R^{3a}$ and $R^{3b}$ are each independently selected from hydrogen, halo, optionally substituted alkyl, optionally substituted alkoxy, or $NR^{10}R^{11}$;

$R^x$ is optionally substituted alkyl, optionally substituted alkenyl, optionally substituted alkynyl, optionally substituted $CQ^aQ^b$-heterocyclyl, optionally substituted $CQ^aQ^b$-bicyclic heterocyclyl, or optionally substituted $CQ^aQ^b$-aryl;

$R^4$ is hydrogen or an optionally substituted alkyl;

$R^5$ is hydrogen or an optionally substituted alkyl;

$R^6$ is optionally substituted alkyl optionally substituted aryl, or optionally substituted heterocyclyl;

$R^7$ is optionally substituted alkyl optionally substituted heterocyclyl, optionally substituted aryl, optionally substituted alkoxy, optionally substituted heterocyclyloxy or optionally substituted aryloxy;

$R^8$ is hydrogen, fluorine or alkyl;

$R^9$ is hydrogen, hydroxy, fluorine or alkyl;

or $R^8$ and $R^9$ together with the carbon to which they are attached form a cycloalkyl ring, optionally containing up to one heteroatom selected from O, S, NH and N-alkyl; or $R^8$ and $R^9$ together with the carbon to which they are attached form a carbonyl group;

$Q^a$ and $Q^b$ are each independently selected from hydrogen, $CH_3$ and fluorine;

$R^{10}$ and $R^{11}$ are each independently selected from hydrogen or alkyl; or $R^{10}$ and $R^{11}$ together with the nitrogen to which they are attached form an aliphatic heterocyclic ring, optionally containing an additional heteroatom selected from O, S, NH and N-alkyl;

and derivatives thereof.

Optional substituents for alkyl alkenyl or alkynyl groups include OH, $CO_2R^y$, $NR^yR^z$, (O), $OC_{1-6}$alkyl or halo, wherein $R^y$ and $R^z$ are independently selected from hydrogen and $C_{1-6}$alkyl. An alkyl group may be substituted by one or more optional substituents, for example up to 5, 4, 3, or 2 optional substituents.

Optional substituents for aryl, heteroaryl or heterocyclyl moieties as a group or part of a group are selected from optionally substituted $C_{1-6}$alkyl, optionally substituted $C_{1-6}$alkoxy and halogen.

Suitably Z is O,

Suitably $R^1$ is $CO_2H$, $CONHSO_2R^6$ or tetrazole. In one aspect $R^1$ is $CO_2H$.

In one aspect $R^{2a}$ and $R^{2b}$ independently represents hydrogen, halo, optionally substituted alkyl optionally substituted alkoxy, CN, $SO_2$alkyl, $SR^5$, or $NO_2$.

Suitably $R^{2a}$ is hydrogen.

Suitably $R^{2b}$ is selected from halogen e.g. Cl.

Preferably $R^{2b}$ is positioned 1,4-relative to the Z substituent and 1,3-relative to the methylene pyridyl moiety.

Suitably $R^{3a}$ and $R^{3b}$ are each independently selected from hydrogen, methyl or chloro. In one aspect $R^{3a}$ is hydrogen and $R^{3b}$ is hydrogen, chloro or methyl. In another aspect $R^{3a}$ and $R^{3b}$ are each hydrogen.

In one embodiment in which X is N and Y is CH, $R^{3a}$ is hydrogen and $R^{3b}$ is methyl, the methyl group is not positioned ortho relative to the $R^1$ group.

When X or Y is CH, the hydrogen may be replaced by $R^{32}$ or $R^{3b}$.

In one embodiment, X is N and Y is CH.

In one aspect, when X is N and Y is CH then $R^{3a}$ is hydrogen and $R^{3b}$ is hydrogen. In another aspect, when X is N and Y is CH then $R^{3a}$ is hydrogen and $R^{3b}$ is $CH_3$ and is positioned on the carbon atom in the para position relative to the $R^1$ group. In another aspect, when X is N and Y is CH then $R^{3a}$ is hydrogen and $R^{3b}$ is chloro and is positioned on the carbon atom in the meta position relative to the $R^1$ group.

Suitably when $R^x$ represents optionally substituted alkyl this group is $C_{3-8}$alkyl, for example 1-methylethyl, 2-methylpropyl, 2-ethylbutyl, cyclopentyl, cyclopropylmethylene, cyclopentylmethylene, and cyclohexylmethylene. In one aspect the alkyl group is unsubstituted.

Suitably when $R^x$ represents optionally substituted alkenyl this group is $C_{3-8}$alkenyl, for example 2-methyl-2-propen-1-yl. In one aspect the alkenyl group is unsubstituted.

Suitably when $R^x$ represents optionally substituted alkynyl this group is $C_{3-8}$alkynyl.

When $R^x$ represents optionally substituted $CQ^aQ^b$-heterocyclyl, optionally substituted $CQ^aQ^b$-bicyclic heterocyclyl or optionally substituted $CQ^aQ^b$-aryl, suitably $R^x$ includes optionally substituted $CH_2$-heterocyclyl, optionally substituted $CH_2$-bicyclic heterocyclyl or optionally substituted $CH_2$-aryl e.g optionally substituted $CH_2$-phenyl. Optional substituents when $R^x$ is $CH_2$-phenyl include one, two or three substituents each independently selected from Cl and F.

In one aspect $R^x$ represents $C_{3-8}$alkyl, $C_{3-8}$alkenyl, or optionally substituted $CH_2$-phenyl.

Suitably $R^4$ includes hydrogen and $C_{1-6}$alkyl. In one aspect $R^4$ is hydrogen or $C_{1-3}$alkyl.

Suitably $R^5$ includes hydrogen and $C_{1-6}$alkyl. In one aspect $R^5$ is hydrogen and $C_{1-3}$alkyl.

Suitably $R^6$ is optionally substituted $C_{1-6}$alkyl, optionally substituted aryl, or optionally substituted heterocyclyl. In one aspect $R^5$ is optionally substituted $C_{1-4}$alkyl, optionally substituted aryl, or optionally substituted heterocyclyl.

When $R^6$ is optionally substituted aryl, suitably it is optionally substituted phenyl.

Suitable optional substituents when $R^6$ is phenyl include halogen, e.g. chloro and bromo, $OC_{1-4}$alkyl, and $NHCOC_{1-4}$alkyl.

When $R^6$ is optionally substituted heterocyclyl in one aspect it is optionally substituted isoxazolyl, e.g. 3,5-dimethylisoxazol-4-yl.

Suitably $R^7$ includes $C_{1-6}$alkyl, heteroaryl, heterocyclyl or phenyl.

Suitably $R^8$ includes hydrogen.

Suitably $R^9$ includes hydrogen.

Suitably $Q^a$ is hydrogen.

Suitably $Q^b$ is hydrogen.

In one aspect the compound of formula (I) is a compound of formula (IA):

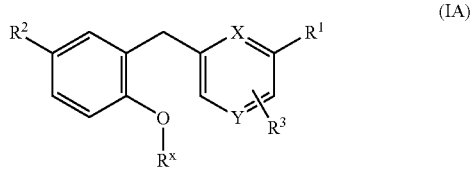

(IA)

wherein:

X is N and Y is CH, or X is CH and Y is N;

$R^1$ is $CO_2H$, $CONHSO_2R^6$, or tetrazole;

$R^2$ is halogen;

$R^3$ is hydrogen, halogen, or optionally substituted alkyl;

$R^x$ is optionally substituted alkyl, optionally substituted alkenyl, optionally substituted alkynyl, optionally substituted $CQ^aQ^b$-heterocyclyl, optionally substituted $CQ^aQ^b$-bicyclic heterocyclyl, or optionally substituted $CQ^aQ^b$-aryl;

$R^6$ is optionally substituted alkyl, optionally substituted aryl, or optionally substituted heterocyclyl; and $Q^a$ and $Q^b$ are each independently selected from hydrogen, $CH_3$ and fluorine; and derivatives thereof.

Optional substituents for alkyl, alkenyl or alkynyl groups include OH, $CO_2R^y$, $NR^yR^z$, (O), $OC_{1-6}$alkyl or halo, wherein $R^y$ and $R^z$ are independently selected from hydrogen and $C_{1-6}$alkyl. An alkyl group may be substituted by one or more optional substituents, for example up to 5, 4, 3, or 2 optional substituents.

Optional substituents for aryl, heteroaryl or heterocyclyl moieties as a group or part of a group are selected from optionally substituted $C_{1-6}$alkyl, optionally substituted $C_{1-6}$alkoxy and halogen.

In one embodiment $R^1$ is $CO_2H$.

In one aspect $R^2$ is chlorine.

Suitably $R^3$ is hydrogen, chloro or methyl, particularly hydrogen.

In one embodiment in which X is N and Y is CH, $R^{3a}$ is hydrogen and $R^{3b}$ is methyl, the methyl group is not positioned ortho relative to the $R^1$ group.

In one embodiment, X is N and Y is CH.

When X or Y is CH, the hydrogen may be replaced by $R^3$.

In one aspect, when X is N and Y is CH then $R^3$ is hydrogen. In another aspect, when X is N and Y is CH then $R^3$ is $CH_3$ and is positioned on the carbon atom in the para position relative to the $R^1$ group. In yet another aspect, when X is N and Y is CH then $R^3$ is chloro and is positioned on the carbon atom in the meta position relative to the $R^1$ group.

Suitably $R^x$ is optionally substituted $C_{3-8}$alkyl, optionally substituted $C_{3-8}$alkenyl, optionally substituted $C_{3-8}$alkynyl, optionally substituted $CQ^aQ^b$-heterocyclyl, optionally substituted $CQ^aQ^b$-bicyclic heterocyclyl, or optionally substituted $CQ^aQ^b$-aryl. In one aspect $R^x$ is optionally substituted $C_{3-8}$alkyl, optionally substituted $C_{3-8}$alkenyl, or optionally substituted $CH_2$-phenyl. In yet another aspect $R^x$ is $C_{3-8}$alkyl, $C_{3-8}$alkenyl, or optionally substituted $CH_2$-phenyl. In a more particular aspect, $R^x$ is optionally substituted $CH_2$-phenyl.

Optional substituents when $R^x$ is substituted $CH_2$-phenyl include one, two or three substituents each independently selected from Cl and F. More particularly, when $R^x$ is substituted $CH_2$-phenyl, the phenyl group may be optionally substituted at the 4-position relative to the methylene moiety with a chlorine atom and at the 2-position relative to the methylene moiety with a fluorine atom.

Suitably $R^6$ is optionally substituted $C_{1-6}$alkyl, optionally substituted phenyl, or optionally substituted heterocyclyl. Suitable optional substituents when $R^6$ is phenyl include halogen, e.g. chloro and bromo, $OC_{1-4}$alkyl, and $NHCOC_{1-4}$alkyl. When $R^6$ is optionally substituted heterocyclyl in one aspect it is optionally substituted isoxazolyl, e.g. 3,5-dimethylisoxazol-4-yl.

Suitably $Q^a$ and $Q^b$ are each hydrogen.

In a more particular aspect, the compound of formula (I) is a compound of formula (IA) wherein:

X is N and Y is CH;

$R^1$ is $CO_2H$, $CONHSO_2R^6$, or tetrazole;

$R^2$ is halogen;

$R^3$ is hydrogen;

$R^x$ is alkyl, alkenyl, or —$CH_2$-aryl, wherein said aryl group is optionally substituted by one or more halogen atoms;

$R^6$ is alkyl, optionally substituted aryl, or optionally substituted heterocyclyl wherein the optional substituents on the aryl and heterocyclyl groups are selected from the group consisting of halogen, $C_{1-6}$alkyl and $C_{1-6}$alkoxy;

and derivatives thereof.

In one embodiment $R^1$ is $CO_2H$.

In another embodiment, $R^2$ is chlorine.

In a further embodiment, $R^x$ represents —$CH_2$-aryl, wherein said aryl group is optionally substituted by one or more halogen atoms, particularly —$CH_2$-phenyl, wherein said phenyl group is optionally substituted by one or more halogen atoms.

Even more particularly, $R^x$ represents $CH_2$-phenyl substituted with one, two or three halogen atoms each independently selected from Cl and F. More particularly, when $R^x$ is substituted $CH_2$-phenyl, the phenyl group may be optionally substituted at the 4-position relative to the methylene moiety with a chlorine atom and at the 2-position relative to the methylene moiety with a fluorine atom.

Compounds of formula (I) include the compounds of examples 1 to 41 and derivatives thereof.

In one embodiment, compounds of the invention do not include:

5-[(5-chloro-2-{[(2,6-difluorophenyl)methyl]oxy}phenyl) methyl]-3-pyridinecarboxylic acid;
6-[(5-Chloro-2-{[(4-chloro-2-fluorophenyl)methyl]oxy}-phenyl)methyl]-N-[(3,5-dichlorophenyl)sulphonyl]-2-pyridinecarboxamide;
6-[(5-Chloro-2-{[(4-chloro-2-fluorophenyl)methyl]oxy}-phenyl)methyl]-N-{[4-methoxyphenyl]sulphonyl}-2-pyridine-carboxamide;
6-[(5-Chloro-2-{[(4-chloro-2-fluorophenyl)methyl] oxy}phenyl)methyl]-3-methyl-2-pyridinecarboxylic acid; and/or
6-({5-Chloro-2-[(1,1-dimethylethyl)oxy]phenyl}methyl)-2-pyridinecarboxylic acid.

In a more particular embodiment, compounds of the invention do not include:

5-[(5-chloro-2-{[(2,6-difluorophenyl)methyl]oxy}phenyl) methyl]-3-pyridinecarboxylic acid;
6-[(5-Chloro-2-{[(4-chloro-2-fluorophenyl)methyl]oxy}-phenyl)methyl]-N-[(3,5-dichlorophenyl)sulphonyl]-2-pyridinecarboxamide; and/or
6-({5-Chloro-2-[(1,1-dimethylethyl)oxy]phenyl}methyl)-2-pyridinecarboxylic acid.

An example of a compound of formula (I) is 6-[(5-chloro-2-{[(4-chloro-2-fluorophenyl)methyl]oxy}phenyl)methyl]-2-pyridinecarboxylic acid or a derivative thereof, particularly a pharmaceutically acceptable derivative thereof. Pharmaceutically acceptable derivatives include salts formed with sodium, methanesulfonic acid or tris(hydroxymethyl)aminomethane (trometamol).

Derivatives of the compound of formula (I) include salts, solvates (including hydrates), solvates (including hydrates) of salts, esters and polymorphs of the compound of formula (I). Derivatives of the compounds of formula (I) include pharmaceutically acceptable derivatives.

It is to be understood that the present invention encompasses all isomers of formula (I) and their pharmaceutically acceptable derivatives, including all geometric, tautomeric and optical forms, and mixtures thereof (e.g. racemic mixtures). Where additional chiral centres are present in compounds of formula (I), the present invention includes within its scope all possible diastereoismers, including mixtures thereof. The different isomeric forms may be separated or resolved one from the other by conventional methods, or any given isomer may be obtained by conventional synthetic methods or by stereospecific or asymmetric syntheses.

The present invention also includes isotopically-labelled compounds, which are identical to the compounds of formula (I), except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine and chlorine such as $^2H$, $^3H$, $^{11}C$, $^{14}C$, $^{18}F$, $^{35}S$, $^{123}I$, and $^{125}I$.

Compounds of the present invention and pharmaceutically acceptable derivatives (e.g. salts) of said compounds that contain the aforementioned isotopes and/or other isotopes of other atoms are within the scope of the present invention. Isotopically-labelled compounds of the present invention, for example those into which radioactive isotopes such as $^3H$ and/or $^{14}C$ are incorporated, are useful in drug and/or substrate tissue distribution assays. $^3H$ and $^{14}C$ are considered useful due to their ease of preparation and detectability. $^{11}C$ and $^{18}F$ isotopes are considered useful in PET (positron emission tomography), and $^{125}I$ isotopes are considered useful in SPECT (single photon emission computerized tomography), all useful in brain imaging. Substitution with heavier isotopes such as $^2H$ can afford certain therapeutic advantages resulting from greater metabolic stability, for example increased in vivo half-life or reduced dosage requirements and, hence, are considered useful in some circumstances. Isotopically labelled compounds of formula (I) of this invention can generally be prepared by carrying out the procedures disclosed in the Schemes and/or in the Examples below, by substituting a readily available isotopically labelled reagent for a non-isotopically labelled reagent.

The following definitions are used herein unless otherwise indicated.

The term "pharmaceutically acceptable derivative" means any pharmaceutically acceptable salt, solvate, ester, or solvate of salt or ester of the compounds of formula (I), or any other compound which upon administration to the recipient is capable of providing (directly or indirectly) a compound of formula (I). In one aspect the term "pharmaceutically acceptable derivative" means any pharmaceutically acceptable salt, solvate or solvate of salt. In an alternative aspect the term "pharmaceutically acceptable derivative" means any pharmaceutically acceptable salt.

It will be appreciated that, for pharmaceutical use, the derivatives referred to above will be pharmaceutically acceptable derivatives, but other derivatives may find use, for example in the preparation of compounds of formula (I) and the pharmaceutically acceptable derivatives thereof.

Pharmaceutically acceptable salts include those described by Berge, Bighley and Monkhouse, *J. Pharm. Sci.*, 1977, 66, 1-19. The term "pharmaceutically acceptable salts" refers to salts prepared from pharmaceutically acceptable bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic bases include salts of primary, secondary, and tertiary amines; substituted amines including naturally occurring substituted amines; and cyclic amines. Particular pharmaceutically acceptable organic bases include arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, procaine, purines, theobromine, triethylamine, trimethylamine, tripropylamine, tris(hydroxymethyl)aminomethane (TRIS, trometamol) and the like. Salts may also be formed from basic ion exchange resins, for example polyamine resins. When the compound of the present invention is basic, salts may be prepared from pharmaceutically acceptable acids, including inorganic and organic acids. Such acids include acetic, benzenesulfonic, benzoic, camphorsulfonic, citric, ethanesulfonic, ethanedisulfonic, fumaric, gluconic, glutamic, hydrobromic, hydrochloric, isethionic, lactic, maleic, malic, mandelic, methanesulfonic, mucic, pamoic, pantothenic, phosphoric, propionic, succinic, sulfuric, tartaric, p-toluenesulfonic acid, and the like.

The compounds of formula (I) may be prepared in crystalline or non-crystalline form, and may be optionally hydrated or solvated. This invention includes in its scope stoichiometric hydrates as well as compounds containing variable amounts of water.

Suitable solvates include pharmaceutically acceptable solvates, such as hydrates.

Solvates include stoichiometric solvates and non-stoichiometric solvates.

The terms "halogen" or "halo" are used to represent fluorine, chlorine, bromine or iodine.

The term "alkyl" as a group or part of a group means a straight, branched or cyclic alkyl group or combinations thereof. Unless hereinbefore defined, examples of alkyl include $C_{1-8}$alkyl, for example methyl, ethyl, n-propyl, iso-propyl, n-butyl, sec-butyl, iso-butyl, t-butyl, pentyl, hexyl, 1,1-dimethylethyl, cyclopropyl, cyclopentyl or cyclohexyl or combinations thereof such as cyclopropylmethylene, cyclohexylmethylene and cyclopentylmethylene.

When used herein the term "cycloalkyl" means a cyclic alkyl group comprising up to eight carbon atoms in a ring.

The term "alkenyl" means linear or branched structures and combinations thereof, of the indicated number of carbon atoms, having at least one carbon-to-carbon double bond, wherein hydrogen may be replaced by an additional carbon to carbon double bond. $C_{3-8}$alkenyl, for example, includes 2-methyl-2-propenyl and the like.

The term "alkynyl" means linear or branched structures and combinations thereof, of the indicated number of carbon atoms, having at least one carbon-to-carbon triple bond. $C_{3-8}$alkynyl, for example, includes propynyl and the like.

The term "alkoxy" as a group or as part of a group means a straight, branched or cyclic chain alkoxy group. Unless hereinbefore defined "alkoxy" includes $C_{1-8}$alkoxy, e.g. methoxy, ethoxy, n-propoxy, iso-propoxy, n-butoxy, sec-butoxy, iso-butoxy, t-butoxy, pentoxy, hexyloxy, cyclopentoxy or cyclohexyloxy. In one aspect "alkoxy" is $C_{1-6}$ alkoxy.

The term "heterocyclyl" as a group or as part of a group means an aromatic or non-aromatic five or six membered ring which contains from 1 to 4 heteroatoms selected from nitrogen, oxygen or sulfur and unsubstituted or substituted by, for example, up to three substituents, preferably one or two substituents. Examples of 5-membered heterocycles include furan, tetrahydrofuran, thiophene, tetrahydrothiophene, pyrrole, pyrroline, pyrrolidine, dioxolane, oxazole, thiazole, imidazole, imidazoline, imidazolidine, pyrazole, pyrazoline, pyrazolidine, isoxazole, isothiazole, oxadiazole, triazole, thiadiazole, and tetrazole. Examples of 6-membered heterocycles include pyran, tetrahydropyran, pyridine, piperidine, dioxane, morpholine, dithiane, thiomorpholine, pyridazine, pyrimidine, pyrazine, piperazine, and triazine.

The term "heterocyclyloxy" as a group or as part of a group refers to an "—O-heterocyclyl" group, wherein the term "heterocyclyl" is as defined above.

The term "aliphatic heterocyclyl" as a group or as part of a group means an aliphatic five or six membered ring which contains 1 or 2 heteroatoms selected from nitrogen, oxygen or sulfur and is unsubstituted or substituted by, for example, up to three substituents, preferably one or two substituents.

The term "aryl" as a group or part of a group means a 5- or 6-membered aromatic ring, for example phenyl, or a 7 to 12 membered bicyclic ring system where at least one of the rings is aromatic, for example naphthyl. An aryl group may be optionally substituted by one or more substituents, for example up to 4, 3 or 2 substituents. Preferably the aryl group is phenyl.

The term "aryloxy" as a group or as part of a group refers to an "—O-aryl" group, wherein the term "aryl" is as defined above.

The term "heteroaryl" as a group or as part of a group means a monocyclic five or six membered aromatic ring, or a fused bicyclic aromatic ring system comprising two of such monocyclic five or six membered aromatic rings. These heteroaryl rings contain one or more heteroatoms selected from nitrogen, oxygen or sulfur, where N-oxides, sulfur oxides and sulfur dioxides are permissible heteroatom substitutions. A heteroaryl group may be optionally substituted by one or more substituents, for example up to 3 or up to 2 substituents. Examples of "heteroaryl" used herein include furyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyrimidinyl, quinolinyl, isoquinolinyl, benzofuryl, benzothienyl, indolyl, and indazolyl.

The term "bicyclic heterocyclyl" when used herein means a fused bicyclic aromatic or non-aromatic bicyclic heterocyclyl ring system comprising up to four, preferably one or two, heteroatoms each selected from oxygen, nitrogen and sulphur. Each ring may have from 4 to 7, preferably 5 or 6, ring atoms. A bicyclic heteroaromatic ring system may include a carbocyclic ring. Examples of bicyclic heterocyclyl groups include quinolinyl, isoquinolinyl, quinoxalinyl, quinazolinyl, pyridopyrazinyl, benzoxazolyl, benzothiophenyl, benzimidazolyl, benzothiazolyl, benzoxadiazolyl, benzthiadiazolyl, indolyl, benztriazolyl or naphthyridinyl.

When the heteroatom nitrogen replaces a carbon atom in an alkyl group, or when nitrogen is present in a heteroaryl, heterocyclyl or bicyclic heterocyclyl group, the nitrogen atom will, where appropriate be substituted by one or two substituents selected from hydrogen and $C_{1-8}$alkyl, preferably hydrogen and $C_{1-6}$alkyl, more preferably hydrogen.

Compounds of formula (I) can be prepared as set forth in the following scheme and in the examples. The following processes form another aspect of the present invention.

For example, compounds of formula (I) wherein $R^1$ is $CO_2H$, hereinafter referred to as compounds of formula (IB), may be prepared by the general route shown in Scheme I below:

Scheme I

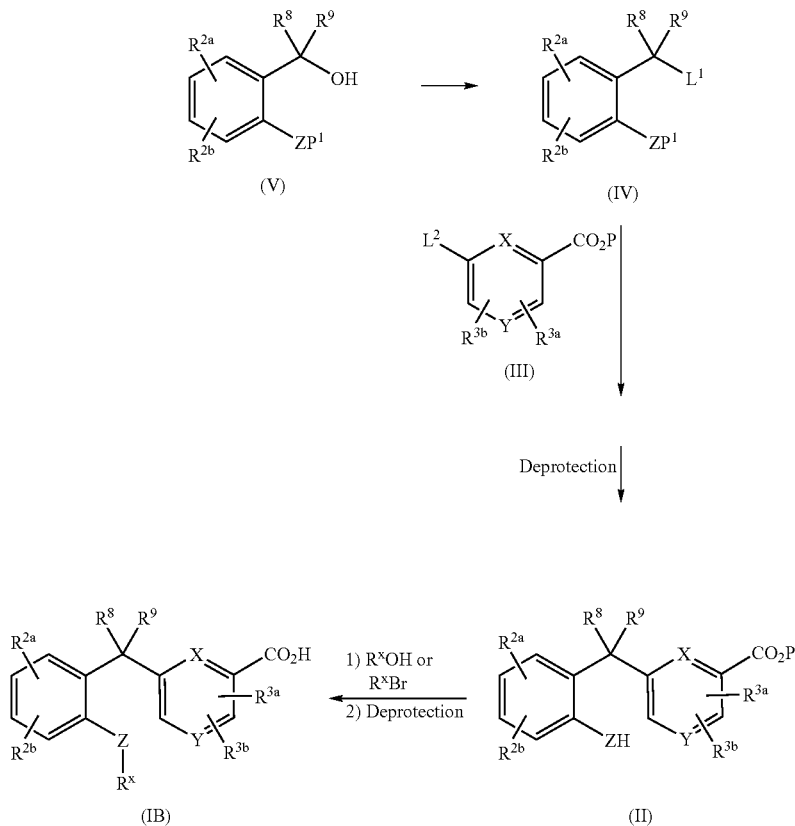

wherein $L^1$ and $L^2$ are halo groups, selected for example from bromo and iodo;

X, Y, Z, $R^{2a}$, $R^{2b}$, $R^{3a}$, $R^{3b}$, $R^8$, $R^9$, and $R^x$ are as defined for compounds of formula (I); and P and $P^1$ are protecting groups.

Compounds of formula (IB) may be prepared from an intermediate of formula (II) by reaction with a suitable source of $R^x$ wherein $R^x$ is as defined for a compound of formula (I). Suitable sources of $R^x$ include $R^x$OH, $R^x$Br, $R^x$OTs and $R^x$OMs. Suitable reaction conditions when the source of $R^x$ is $R^x$Br include heating in the presence of a base e.g. potassium carbonate in a suitable solvent e.g. acetone or N,N-dimethylformamide, followed by removal of protecting group P. Alternatively the compound of formula (IB) may be prepared by the reaction with $R^x$OH under Mitsunobu conditions ($Ph_3P$/diisopropylazodicarboxylate) (O. Mitsunobu et al., *Bull. Chem. Soc. Japan,* 40, 935 (1967); O. Mitsunobu, Y. Yamada, *ibid.* 2380), followed by removal of the protecting group P.

Suitable protecting groups will be known to the skilled person. Suitably P is $C_{1-4}$alkyl or optionally substituted benzyl.

Suitable deprotection methods will be known to the skilled person. Conditions for the deprotection of an ester to give the corresponding carboxylic acid are known to those skilled in the art and include heating in the presence of a suitable base, e.g. aqueous sodium hydroxide, in a solvent e.g. an alcohol.

Suitable conditions for the reaction of a compound of formula (III) with a compound of formula (IV) to give a compound of formula (II) include treating the compound of formula (IV) with activated zinc in a suitable solvent, e.g. tetrahydrofuran, and adding the resulting reagent to the compound of formula (III) in the presence of tetrakis(triphenylphosphine)palladium(0).

Suitably $P^1$ is benzyl when Z is O. Removal of the protecting group $P^1$ can be achieved by heating with sodium methanethiolate in N,N-dimethylformamide. The skilled person will recognise that this procedure may also result in the loss of the P group. A protecting group may be replaced by conventional means.

Alternatively compounds of formula (I) wherein $R^1$ is $CO_2H$ [compounds of formula (IB)], may be prepared by the general route shown in Scheme II:

Scheme II

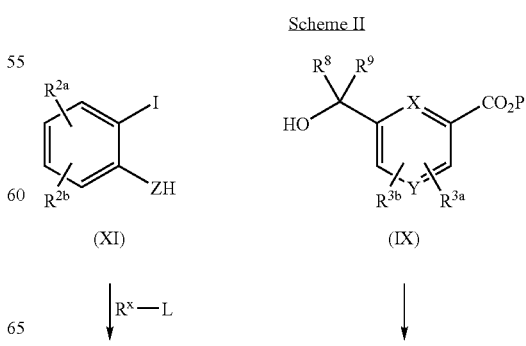

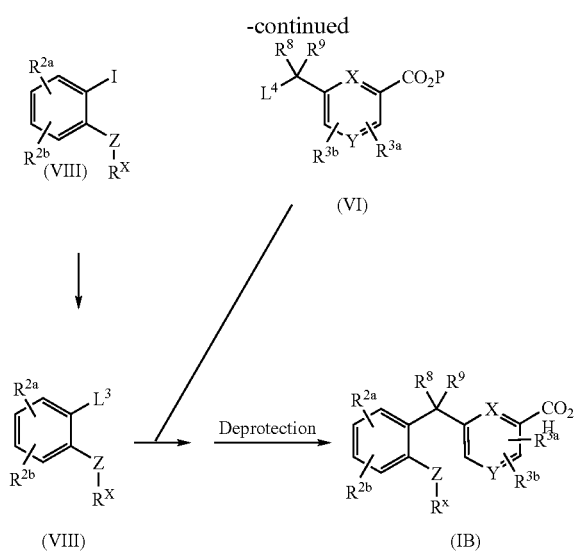

wherein P is a protecting group (e.g. methyl or ethyl), L is a leaving group (e.g. Br), $L^3$ is an activating group e.g. boronic acid or a boronic ester, $L^4$ is a leaving group (e.g. Cl), and X, Y, Z, $R^{2a}$, $R^{2b}$, $R^{3a}$, $R^{3b}$, $R^8$, $R^9$, and $R^x$ are as defined for compounds of formula (I).

Compounds of formula (IB) may be prepared by reaction of an intermediate of formula (VI) with an intermediate of formula (VII). Suitably the intermediate of formula (VII) is a boronic acid [$L^3$ is $B(OH)_2$] or a boronic ester [$L^3$ is e.g. 4,4,5,5,-tetramethyl-1,3,2-dioxaborolane]. Suitably $L^4$ of the compound of formula (VI) is chloro. Suitable reaction conditions when (VII) is a boronic acid or ester and $L^4$ of the compound of formula (VI) is chloro include heating the intermediates in the presence of tetrakis(triphenylphosphine)palladium(0) and a base, e.g. potassium carbonate, in a suitable solvent system (e.g. from 1:1 to 15:1 toluene/ethanol), followed by removal of protecting group P.

Intermediates of formula (VII) when $L^3$ is $B(OH)_2$ may be prepared according to conventional methods from the corresponding iodobenzene of formula (VI II) by treatment with iso-propylmagnesium bromide followed by trimethyl borate in a suitable solvent such as tetrahydrofuran under anhydrous conditions in an inert atmosphere. Intermediates of formula (VII) when $L^3$ is a boronic ester may be prepared under similar conditions, and by using, for example, isopropyltetramethyldioxaborolane instead of trimethyl borate.

Intermediates of formula (VIII) may be prepared, for example, by the reaction of a compound of formula (XI) with $R^xL$. Suitable reaction conditions include heating the compounds together in the presence of a base (e.g. potassium carbonate) in a suitable solvent, for example acetone. The skilled person will appreciate that when Z is SO or $SO_2$, the alkylation step is carried out when Z is S, and the sulfur is then oxidised to the required oxidation state by conventional means at an appropriate stage in the synthesis.

Intermediates of formula (VI) where $L^4$ is chloro may be prepared, for example, from the corresponding hydroxy intermediate of formula (IX). Suitable reaction conditions include reacting the compound of formula (IX) with thionyl chloride in a suitable solvent such as dichloromethane.

It will be recognised to those skilled in the art that the compounds of formula (I) wherein $R^1$ is other than $CO_2H$ can be derived from the carboxylic acid (IB). Compounds wherein $R^1$ is an acylsulfonamide, can be prepared by activation of the carboxylic acid, for example by forming the acid chloride (for example by reaction of the carboxylic acid with thionyl chloride) followed by reaction with a sulfonamide respectively. Other derivatives may be accessed by using the Curtius reaction (P. A. S. Smith, Org. React. 3, 337-449 (1946) and J. H. Saunders, R. J. Slocombe, Chem. Rev. 43, 205 (1948)), followed by deprotection of the resulting carbamate and reaction with a carboxylic acid derivative such as an acid chloride. Compounds where a methylene group has been inserted between the pyridine ring and the carboxylic acid group may be prepared using the Arndt-Eistert reaction (F. Arndt, B. Eistert, Ber. 68, 200 (1935), W. E. Bachmann, W. S. Struve, Org. React. 1, 38-62 (1942), G. B. Gill, Comp. Org. Syn. 3, 888-889 (1991), T. Aoyama, Tetrahedron Letters, 21, 4461 (1980)). It will be recognised to those skilled in the art that tetrazoles may be formed from carboxylic acids by converting the carboxylic acid to the primary amides, for example by reaction with sulfonyl chloride followed by ammonia, followed by dehydration of the amide to the nitrile, for example by heating in phosphorous oxychloride, followed by reaction with azide.

Accordingly the present invention also provides a process for the preparation of a compound of formula (I) or a derivative thereof:

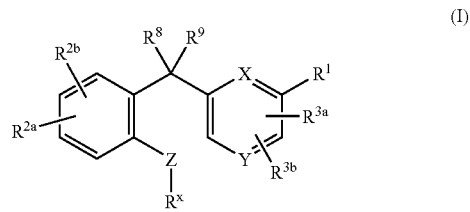

(I)

wherein:

X is N and Y is CH, or X is CH and Y is N;

Z is O, S, SO or $SO_2$;

$R^1$ is $CO_2H$, $CONHSO_2R^6$, $CH_2CO_2H$, $NR^4COR^7$, tetrazole or $CH_2$tetrazole;

$R^{2a}$ and $R^{2b}$ are each independently selected from hydrogen, halo, CN, $SO_2$alkyl, $SR^5$, $NO_2$, optionally substituted alkyl optionally substituted alkoxy, optionally substituted aryl, and optionally substituted heteroaryl;

$R^{3a}$ and $R^{3b}$ are each independently selected from hydrogen, halo, optionally substituted alkyl optionally substituted alkoxy, or $NR^{10}R^{11}$;

$R^x$ is optionally substituted alkyl optionally substituted alkenyl, optionally substituted alkynyl, optionally substituted $CQ^aQ^b$-heterocyclyl, optionally substituted $CQ^aQ^b$-bicyclic heterocyclyl, or optionally substituted $CQ^aQ^b$-aryl;

$R^4$ is hydrogen or an optionally substituted alkyl;

$R^5$ is hydrogen or an optionally substituted alkyl;

$R^6$ is optionally substituted alkyl optionally substituted aryl, or optionally substituted heterocyclyl;

$R^7$ is optionally substituted alkyl optionally substituted heterocyclyl, optionally substituted aryl, optionally substituted alkoxy, optionally substituted heterocyclyloxy or optionally substituted aryloxy;

$R^8$ is hydrogen, fluorine or alkyl;

$R^9$ is hydrogen, hydroxy, fluorine or alkyl;

or $R^8$ and $R^9$ together with the carbon to which they are attached form a cycloalkyl ring, optionally containing up to one heteroatom selected from O, S, NH and N-alkyl; or $R^8$ and $R^9$ together with the carbon to which they are attached form a carbonyl group;

$Q^a$ and $Q^b$ are each independently selected from hydrogen, $CH_3$ and fluorine;

$R^{10}$ and $R^{11}$ are each independently selected from hydrogen or alkyl; or $R^{10}$ and $R^{11}$ together with the nitrogen to which they are attached form an aliphatic heterocyclic ring, optionally containing an additional heteroatom selected from O, S, NH and N-alkyl;

comprising:

reacting a compound of formula (II):

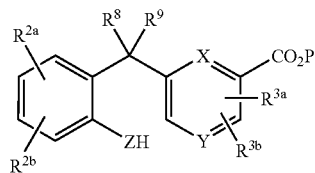

(II)

wherein P is a protecting group and Z, $R^8$, $R^9$, $R^{2a}$, $R^{2b}$, $R^{3a}$ and $R^{3b}$ are as defined above for a compound of formula (I);

with a compound $R^x$-L;

wherein $R^x$ is as defined above for a compound of formula (I), and L is Cl, Br or OH;

and if required, and in any order;

converting one group $R^1$ to another group $R^1$; and/or effecting deprotection; and/or forming a derivative thereof.

Optional substituents for alkyl, alkenyl or alkynyl groups include OH, $CO_2R^y$, $NR^yR^z$, (O), $OC_{1-6}$alkyl or halo, wherein $R^y$ and $R^z$ are independently selected from hydrogen and $C_{1-6}$alkyl. An alkyl group may be substituted by one or more optional substituents, for example up to 5, 4, 3, or 2 optional substituents.

Optional substituents for aryl, heteroaryl or heterocyclyl moieties as a group or part of a group are selected from optionally substituted $C_{1-6}$alkyl, optionally substituted $C_{1-6}$alkoxy and halogen.

In addition the present invention also provides a process for the preparation of a compound of formula (I) or a derivative thereof:

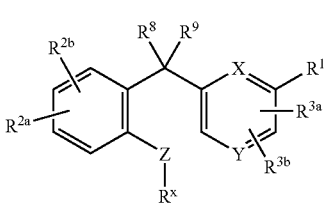

(I)

wherein:

X is N and Y is CH, or X is CH and Y is N;

Z is O, S, SO or $SO_2$;

$R^1$ is $CO_2H$, $CONHSO_2R^6$, $CH_2CO_2H$, $NR^4COR^7$, tetrazole or $CH_2$tetrazole;

$R^{2a}$ and $R^{2b}$ are each independently selected from hydrogen, halo, CN, $SO_2$alkyl, $SR^5$, $NO_2$, optionally substituted alkyl, optionally substituted alkoxy, optionally substituted aryl, and optionally substituted heteroaryl;

$R^{3a}$ and $R^{3b}$ are each independently selected from hydrogen, halo, optionally substituted alkyl, optionally substituted alkoxy, or $NR^{10}R^{11}$;

$R^x$ is optionally substituted alkyl, optionally substituted alkenyl, optionally substituted alkynyl, optionally substituted $CQ^aQ^b$-heterocyclyl, optionally substituted $CQ^aQ^b$-bicyclic heterocyclyl, or optionally substituted $CQ^aQ^b$-aryl;

$R^4$ is hydrogen or an optionally substituted alkyl;

$R^5$ is hydrogen or an optionally substituted alkyl;

$R^6$ is optionally substituted alkyl, optionally substituted aryl, or optionally substituted heterocyclyl;

$R^7$ is optionally substituted alkyl optionally substituted heterocyclyl, optionally substituted aryl, optionally substituted alkoxy, optionally substituted heterocyclyloxy or optionally substituted aryloxy;

$R^8$ is hydrogen, fluorine or alkyl;

$R^9$ is hydrogen, hydroxy, fluorine or alkyl;

or $R^8$ and $R^9$ together with the carbon to which they are attached form a cycloalkyl ring, optionally containing up to one heteroatom selected from O, S, NH and N-alkyl; or $R^8$ and $R^9$ together with the carbon to which they are attached form a carbonyl group;

$Q^a$ and $Q^b$ are each independently selected from hydrogen, $CH_3$ and fluorine;

$R^{10}$ and $R^{11}$ are each independently selected from hydrogen or alkyl; or $R^{10}$ and $R^{11}$ together with the nitrogen to which they are attached form an aliphatic heterocyclic ring, optionally containing an additional heteroatom selected from O, S, NH and N-alkyl;

comprising:

reacting a compound of formula (VII):

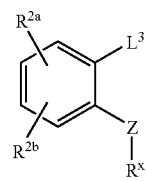

(VII)

wherein $L^3$ is an activating group and Z, $R^x$, $R^{2a}$, and $R^{2b}$ are as defined above for a compound of formula (I);

with a compound of formula (VI):

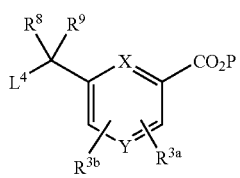

(VI)

wherein P is a protecting group and X, Y, $R^8$, $R^9$, $R^{3a}$ and $R^{3b}$ are as defined above for a compound of formula (I), and $L^4$ is a leaving group;

and if required, and in any order;

converting one group $R^1$ to another group $R^1$; and/or effecting deprotection; and/or forming a derivative thereof.

Optional substituents for alkyl alkenyl or alkynyl groups include OH, $CO_2R^y$, $NR^yR^z$, (O), $OC_{1-6}$alkyl or halo, wherein $R^y$ and $R^z$ are independently selected from hydrogen and $C_{1-6}$alkyl. An alkyl group may be substituted by one or more optional substituents, for example up to 5, 4, 3, or 2 optional substituents.

Optional substituents for aryl, heteroaryl or heterocyclyl moieties as a group or part of a group are selected from optionally substituted $C_{1-6}$alkyl, optionally substituted $C_{1-6}$alkoxy and halogen.

Compounds of formula $R^x$-L wherein L is OH, Br or Cl and $R^x$ is as defined for compounds of formula (I) are commercially available, or may be readily prepared by known transformations of commercially available compounds.

Compounds of formula (III):

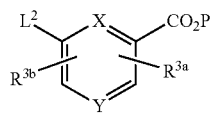

(III)

wherein $R^{3a}$, $R^{3b}$, X and Y are as defined for compounds of formula (I), $L^2$ is halo e.g. Br or Cl and P is a protecting group are commercially available, or may be readily made by known transformations from commercially available intermediates.

Compounds of formula (V):

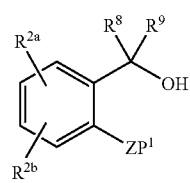

(V)

wherein $P^1$ is a protecting group, Z, $R^{2a}$, $R^{2b}$, $R^8$, and $R^9$ are as defined for compounds of formula (I) are commercially available, or may be prepared from commercially available intermediates by conventional methods such as those described in the examples below. For example processes for the preparation of 2-(hydroxymethyl)phenols are described in W. A. Sheppard, *J. Org. Chem.*, 1968, 33, 3297-3306.

Compounds of formula (IX):

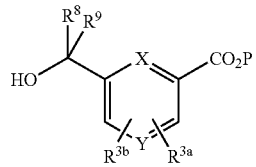

(IX)

wherein X, Y, $R^8$, $R^9$, $R^{3a}$ and $R^{3b}$ are as defined above for compounds of formula (I) and P is a protecting group (e.g. methyl or ethyl) may be prepared by conventional methods known to the skilled person. When $R^8$ and $R^9$ are both hydrogen the compound of formula (IX) may be prepared from the corresponding pyridine dicarboxylate by treatment with sodium borohydride in a suitable solvent such as ethanol. Pyridine dicarboxylates are commercially available, or may be prepared from commercially available intermediates by conventional means. For example a pyridine dicarboxylate may be prepared from a pyridine dicarboxylic acid by treating with concentrated sulfuric acid in the appropriate alcohol, e.g. ethanol.

Compounds of formula (XI):

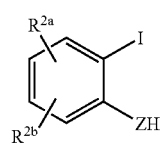

(XI)

wherein Z, $R^{2a}$ and $R^{2b}$ are as defined above for compounds of formula (I) are commercially available or may be prepared from commercially available starting materials by conventional methods known to the skilled person. For example, Iodophenols may be prepared by treatment of the corresponding anisole with boron tribromide in a suitable solvent such as dichloromethane. Suitable anisoles are commercially available.

Certain substituents in any of the reaction intermediates and compounds of formula (I) may be converted to other substituents by conventional methods known to those skilled in the art. Examples of such transformations include the hydrolysis of esters and esterification of carboxylic acids. Such transformations are well known to those skilled in the art and are described in for example, Richard Larock, *Comprehensive Organic Transformations,* 2nd edition, Wiley-VCH, ISBN 0-471-19031-4.

It will be appreciated by those skilled in the art that it may be necessary to protect certain reactive substituents during some of the above procedures. The skilled person will recognise when a protecting group is required. Standard protection and deprotection techniques, such as those described in Greene T. W. 'Protective groups in organic synthesis', New York, Wiley (1981), can be used. For example, carboxylic acid groups can be protected as esters. Deprotection of such groups is achieved using conventional procedures known in the art. It will be appreciated that protecting groups may be interconverted by conventional means.

The compounds of the invention bind to the $EP_1$ receptor and are antagonists of this receptor. They are therefore considered useful in treating conditions mediated by the action of $PGE_2$ at $EP_1$ receptors.

One condition mediated by the action of $PGE_2$ at $EP_1$ receptors is pain, including acute pain, chronic pain, chronic articular pain, musculoskeletal pain, neuropathic pain, inflammatory pain, visceral pain, pain associated with cancer, pain associated with migraine, tension headache and cluster headaches, pain associated with functional bowel disorders, lower back and neck pain, pain associated with sprains and strains, sympathetically maintained pain; myositis, pain associated with influenza or other viral infections such as the common cold, pain associated with rheumatic fever, pain associated with myocardial ischemia, post operative pain, headache, toothache and dysmenorrhea.

Chronic articular pain conditions include rheumatoid arthritis, osteoarthritis, rheumatoid spondylitis, gouty arthritis and juvenile arthritis.

Pain associated with functional bowel disorders includes non-ulcer dyspepsia, non-cardiac chest pain and irritable bowel syndrome.

Neuropathic pain syndromes include: diabetic neuropathy, sciatica, non-specific lower back pain, multiple sclerosis pain, fibromyalgia, HIV-related neuropathy, post-herpetic neuralgia, trigeminal neuralgia, and pain resulting from physical trauma, amputation, cancer, toxins or chronic inflammatory conditions. In addition, neuropathic pain conditions include pain associated with normally non-painful sensations such as "pins and needles" (paraesthesias and dysesthesias), increased sensitivity to touch (hyperesthesia), painful sensation following innocuous stimulation (dynamic, static, thermal or cold allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

Other conditions mediated by the action of $PGE_2$ at $EP_1$ receptors include fever, inflammation, immunological diseases, abnormal platelet function diseases (e.g. occlusive vascular diseases), impotence or erectile dysfunction; bone disease characterised by abnormal bone metabolism or resorbtion; hemodynamic side effects of non-steroidal anti-inflammatory drugs (NSAID's) and cyclooxygenase-2 (COX-2) inhibitors, cardiovascular diseases; neurodegenerative diseases and neurodegeneration, neurodegeneration following trauma, tinnitus, dependence on a dependence-inducing agent such as opioids (e.g. morphine), CNS depressants (e.g. ethanol), psychostimulants (e.g. cocaine) and nicotine; complications of Type I diabetes, kidney dysfunction, liver dysfunction (e.g. hepatitis, cirrhosis), gastrointestinal dysfunction (e.g. diarrhoea), colon cancer, overactive bladder and urge incontenance.

Inflammatory conditions include skin conditions (e.g. sunburn, burns, eczema, dermatitis, psoriasis), ophthalmic diseases such as glaucoma, retinitis, retinopathies, uveitis and of acute injury to the eye tissue (e.g. conjunctivitis), inflammatory lung disorders (e.g. asthma, bronchitis, emphysema, allergic rhinitis, respiratory distress syndrome, pigeon fancier's disease, farmer's lung, chronic obstructive pulmonary disease (COPD); gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastrointestinal reflux disease); organ transplantation and other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, gingivitis, myocardial ischemia, pyrexia, systemic lupus erythematosus, polymyositis, tendinitis, bursitis, and Sjogren's syndrome.

Immunological diseases include autoimmune diseases, immunological deficiency diseases or organ transplantation. The compounds of formula (I) are also effective in increasing the latency of HIV infection Bone diseases characterised by abnormal bone metabolism or resorbtion include osteoporosis (especially postmenopausal osteoporosis), hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, cancer cacchexia, calculosis, lithiasis (especially urolithiasis), solid carcinoma, gout and ankylosing spondylitis, tendinitis and bursitis.

Cardiovascular diseases include hypertension or myocardiac ischemia; functional or organic venous insufficiency; varicose therapy; haemorrhoids; and shock states associated with a marked drop in arterial pressure (e.g. septic shock).

Neurodegenerative diseases include dementia, particularly degenerative dementia (including senile dementia, Alzheimers disease, Pick's disease, Huntingdon's chorea, Parkinson's disease and Creutzfeldt-Jakob disease, ALS, motor neuron disease); vascular dementia (including multi-infarct dementia); as well as dementia associated with intracranial space occupying lesions; trauma; infections and related conditions (including HIV infection); metabolism; toxins; anoxia and vitamin deficiency; and mild cognitive impairment associated with ageing, particularly Age Associated Memory Impairment.

The compounds of formula (I) are also considered useful in the treatment of neuroprotection and in the treatment of neurodegeneration following trauma such as stroke, cardiac arrest, pulmonary bypass, traumatic brain injury, spinal cord injury or the like.

Complications of Type 1 diabetes include diabetic microangiopathy, diabetic retinopathy, diabetic nephropathy, macular degeneration, glaucoma, nephrotic syndrome, aplastic anaemia, uveitis, Kawasaki disease and sarcoidosis.

Kidney dysfunction includes nephritis, particularly mesangial proliferative glomerulonephritis and nephritic syndrome.

The compounds of formula (I) are also considered useful for the preparation of a drug with diuretic action.

It is to be understood that reference to treatment includes both treatment of established symptoms and prophylactic treatment, unless explicitly stated otherwise.

According to a further aspect of the invention, we provide a compound of formula (I) or a pharmaceutically acceptable derivative thereof for use in human or veterinary medicine.

According to another aspect of the invention, we provide a compound of formula (I) or a pharmaceutically acceptable derivative thereof for use in the treatment of a condition which is mediated by the action of $PGE_2$ at $EP_1$ receptors.

According to a further aspect of the invention, we provide a method of treating a human or animal subject suffering from a condition which is mediated by the action of $PGE_2$ at $EP_1$ receptors which comprises administering to said subject an effective amount of a compound of formula (I) or a pharmaceutically acceptable derivative thereof.

According to a further aspect of the invention we provide a method of treating a human or animal subject suffering from a pain, inflammatory, immunological, bone, neurodegenerative or renal disorder, which method comprises administering to said subject an effective amount of a compound of formula (I) or a pharmaceutically acceptable derivative thereof.

According to a yet further aspect of the invention we provide a method of treating a human or animal subject suffering from inflammatory pain, neuropathic pain or visceral pain which method comprises administering to said subject an effective amount of a compound of formula (I) or a pharmaceutically acceptable derivative thereof.

According to another aspect of the invention, we provide the use of a compound of formula (I) or a pharmaceutically acceptable derivative thereof for the manufacture of a medicament for the treatment of a condition which is mediated by the action of $PGE_2$ at $EP_1$ receptors.

According to another aspect of the invention we provide the use of a compound of formula (I) or a pharmaceutically acceptable derivative thereof for the manufacture of a medicament for the treatment or prevention of a condition such as a pain, inflammatory, immunological, bone, neurodegenerative or renal disorder.

According to another aspect of the invention we provide the use of a compound of formula (I) or a pharmaceutically acceptable derivative thereof for the manufacture of a medicament for the treatment or prevention of a condition such as inflammatory pain, neuropathic pain or visceral pain.

The compounds of formula (I) and their pharmaceutically acceptable derivatives are conveniently administered in the form of pharmaceutical compositions. Such compositions may conveniently be presented for use in conventional manner in admixture with one or more physiologically acceptable carriers or excipients.

Thus, in another aspect of the invention, we provide a pharmaceutical composition comprising a compound of formula (I) or a pharmaceutically acceptable derivative thereof.

A proposed daily dosage of compounds of formula (I) or their pharmaceutically acceptable derivatives for the treatment of man is from 0.01 to 80 mg/kg body weight, more particularly 0.01 to 30 mg/kg body weight per day, for example 0.1 to 10 mg/kg body weight per day, which may be administered as a single or divided dose, for example one to four times per day. The dose range for adult human beings is generally from 8 to 4000 mg/day, more particularly from 8 to 2000 mg/day, such as from 20 to 1000 mg/day, for example 35 to 200 mg/day.

The precise amount of the compounds of formula (I) administered to a host, particularly a human patient, will be the responsibility of the attendant physician. However, the dose employed will depend on a number of factors including the age and sex of the patient, the precise condition being treated and its severity, and the route of administration.

The compounds of formula (I) and their pharmaceutically acceptable derivatives may be formulated for administration in any suitable manner. They may be formulated for administration by inhalation or for oral, topical, transdermal or parenteral administration. The pharmaceutical composition may be in a form such that it can effect controlled release of the compounds of formula (I) and their pharmaceutically acceptable derivatives.

For oral administration, the pharmaceutical composition may take the form of, for example, tablets (including sublingual tablets), capsules, powders, solutions, syrups or suspensions prepared by conventional means with acceptable excipients.

For transdermal administration, the pharmaceutical composition may be given in the form of a transdermal patch, such as a transdermal iontophoretic patch.

For parenteral administration, the pharmaceutical composition may be given as an injection or a continuous infusion (e.g. intravenously, intravascularly or subcutaneously). The compositions may take such forms as suspensions, solutions or emulsions in oily or aqueous vehicles and may contain formulatory agents such as suspending, stabilising and/or dispersing agents. For administration by injection these may take the form of a unit dose presentation or as a multidose presentation preferably with an added preservative. Alternatively for parenteral administration the active ingredient may be in powder form for reconstitution with a suitable vehicle.

The compounds of the invention may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

The $EP_1$ receptor compounds for use in the instant invention may be used in combination with other therapeutic agents, for example COX-2 (cyclooxygenase-2) inhibitors, such as celecoxib, deracoxib, rofecoxib, valdecoxib, parecoxib, COX-189 or 2-(4-ethoxy-phenyl)-3-(4-methanesulfonyl-phenyl)-pyrazolo[1,5-b]pyridazine (WO99/012930); 5-lipoxygenase inhibitors; NSAIDs (non-steroidal anti-inflammatory drugs) such as diclofenac, indomethacin, nabumetone or ibuprofen; leukotriene receptor antagonists; DMARDs (disease modifying anti-rheumatic drugs) such as methotrexate; adenosine A1 receptor agonists; sodium channel blockers, such as lamotrigine; NMDA (N-methyl-D-aspartate) receptor modulators, such as glycine receptor antagonists; ligands for the $\alpha_2\delta$-subunit of voltage gated calcium channels, such as gabapentin and pregabalin; tricyclic antidepressants such as amitriptyline; neurone stabilising antiepileptic drugs; mono-aminergic uptake inhibitors such as venlafaxine; opioid analgesics; local anaesthetics; 5HT$_1$ agonists, such as triptans, for example sumatriptan, naratriptan, zolmitriptan, eletriptan, frovatriptan, almotriptan or rizatriptan; nicotinic acetyl choline (nACh) receptor modulators; glutamate receptor modulators, for example modulators of the NR2B subtype; $EP_4$ receptor ligands; $EP_2$ receptor ligands; $EP_3$ receptor ligands; $EP_4$ agonists and $EP_2$ agonists; $EP_4$ antagonists; $EP_2$ antagonists and $EP_3$ antagonists; cannabanoid receptor ligands; bradykinin receptor ligands; vanilloid receptor ligand; and purinergic receptor ligands, including antagonists at $P2X_3$, $P2X_{2/3}$, $P2X_4$, $P2X_7$ or $P2X_{4/7}$. When the compounds are used in combination with other therapeutic agents, the compounds may be administered either sequentially or simultaneously by any convenient route.

Additional COX-2 inhibitors are disclosed in U.S. Pat. No. 5,474,995 U.S. Pat. No. 5,633,272; U.S. Pat. No. 5,466,823, U.S. Pat. No. 6,310,099 and U.S. Pat. No. 6,291,523; and in WO 96/25405, WO 97/38986, WO 98/03484, WO 97/14691, WO99/12930, WO00/26216, WO00/52008, WO00/38311, WO01/58881 and WO02/18374.

The invention thus provides, in a further aspect, a combination comprising a compound of formula (I) or a pharmaceutically acceptable derivative thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

In addition to activity at the $EP_1$ receptor, certain compounds of the present invention and pharmaceutically acceptable derivatives thereof exhibit antagonism of the TP receptor and are therefore indicated to be useful in treating conditions mediated by the action of thromboxane at the TP receptor. Conditions mediated by the action of thromboxane at the TP receptor include renal disorders, asthma, or gastric lesions.

In certain situations it is envisaged that the administration of a compound exhibiting antagonism of TP receptors in combination with a compound exhibiting antagonism of $EP_1$ receptors may be advantageous.

Certain compounds of the invention are selective for $EP_1$ over $EP_3$.

No toxicological effects have currently been observed with the compounds of the invention.

All publications, including but not limited to patents and patent applications, cited in this specification are herein incorporated by reference as if each individual publication were specifically and individually indicated to be incorporated by reference herein as though fully set forth.

The following non-limiting Examples illustrate the preparation of pharmacologically active compounds of the invention.

EXAMPLES

Abbreviations

AcOH, acetic acid, Bn (benzyl), Bu, Pr, Me, Et (butyl, propyl, methyl, ethyl), DMSO (dimethyl sulfoxide), DCM/MDC (dichloromethane), DME (ethylene glycol dimethyl ether), DMF (N,N-dimethylformamide), EDTA (ethylenediaminetetraacetic acid), EtOAc (ethyl acetate), EtOH (ethanol), HPLC (High pressure liquid chromatography), IPA (isopropanol), LCMS (Liquid chromatography/Mass spectroscopy), MDAP (Mass Directed Auto Preparation), MeOH (methanol), ML (mother liquor), NMR (Nuclear Magnetic Resonance (spectrum)), NMP (n-methylpyrrolidone), Ph (phenyl), pTSA (para-toluene sulphonic acid), RT/Rt (retention time), SM (starting material), SPE (Solid Phase Extraction—silica cartridge chromatography), TBAF (tetrabutylammonium fluoride), TBME (tertiary butyl methyl ether), THF (tetrahydrofuran), s, d, dd, t, q, m, br (singlet, doublet, double doublet, triplet, quartet, multiplet, broad.)

Purification of Reaction Products

Conventional techniques may be used herein for work up of reactions and purification of the products of the Examples.

References in the Examples below relating to the drying of organic layers or phases may refer to drying the solution over magnesium sulfate or sodium sulfate and filtering off the drying agent in accordance with conventional techniques. Products may generally be obtained by removing the solvent by evaporation under reduced pressure.

Purification of the Examples may be carried out by conventional methods such as chromatography and/or recrystalisation using suitable solvents. Chromatographic methods are known to the skilled person and include e.g. column chromatography, flash chromatography, HPLC (high performance liquid chromatography), and MDAP (mass directed autopreparation).

The term "Biotage" when used herein refers to commercially available pre-packed silica gel cartridges.

LCMS

The following conditions were used for LCMS in the preparation of the examples.

Column: 3.3 cm×4.6 mm ID, 3 μm ABZ+PLUS

Flow Rate: 3 ml/min

Injection Volume: 5 μl

Temp: Room temperature

UV Detection Range: 215 to 330 nm

Solvents:
A: 0.1% Formic Acid+10 mMolar Ammonium Acetate.
B: 95% Acetonitrile+0.05% Formic Acid

| | Gradient: | |
| --- | --- | --- |
| Time | A % | B % |
| 0.00 | 100 | 0 |
| 0.70 | 100 | 0 |
| 4.20 | 0 | 100 |
| 5.30 | 0 | 100 |
| 5.50 | 100 | 0 |

All retention times are measured in minutes.

Preparation of Intermediates

{5-Chloro-2-[(phenylmethyl)oxy]phenyl}methanol

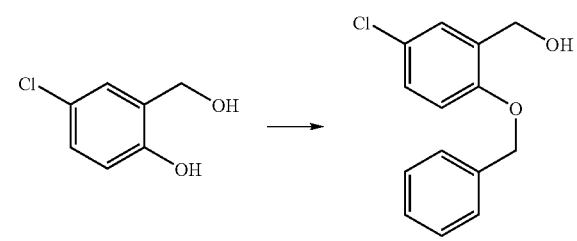

4-Chloro-2-(hydroxymethyl)phenol (5 g, 31 mmol), benzyl bromide (3.74 ml, 31 mmol), and potassium carbonate (4.78 g, 34 mmol) were refluxed in acetone (30 ml) for two hours. TLC showed no more SM (starting material). Cooled down, filtered off the solid and vacuumed down (the filtrate) to give a clear oil (8.2 g).

$^1$H NMR (CDCl$_3$) δ: 2.29 (1H, t), 4.68 (2H, d, J=6.4 Hz), 5.07 (2H, s), 6.84 (1H, d, J=8.6 Hz), 7.6 (1H, d, J=8.6 Hz), 7.30-7.39 (6H, m).

4-Chloro-2-(bromomethyl)phenyl phenylmethyl ether

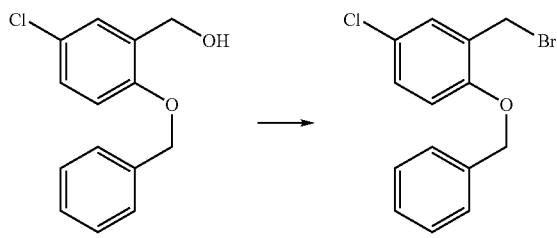

{5-chloro-2-[(phenylmethyl)oxy]phenyl}methanol (8.2 g, 33 mmol) was dissolved in dry dichloromethane under nitrogen and cooled to −10° C. Phosphorus tribromide (3.12 ml, 33 mmol) in dry dichloromethane (15 ml) was added slowly. The mixture was left at −10° C. for 15 mins, then stirred at room temperature overnight. TLC showed no more starting material. The mixture was then quenched with a saturated sodium hydrogen carbonate solution added very slowly. The mixture was diluted with dichloromethane and brine was added to aid separation. The organic phase was washed with water (×2), then dried (MgSO$_4$) and evaporated. The residue was purified (50 g SPE column). Product comes off using 5% ethyl acetate in isohexane. White-ish solid obtained (8.1 g).

$^1$H NMR (CDCl$_3$) δ: 4.53 (2H, s), 5.14 (2H, s), 6.84 (1H, d, J=8.8 Hz), 7.21 (1H, dd, J=8.8, 2.6 Hz), 7.32-7.47 (6H, m).

Ethyl 6-[(5-chloro-2-hydroxyphenyl)methyl]-2-pyridinecarboxylate

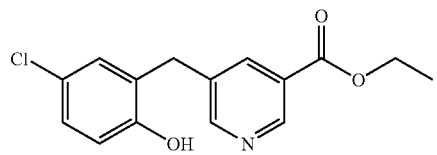

(*J. Org. Chem.*, 1988, 53, 2392-94)

Activation of Zinc Dust

A suspension of zinc (2.5 g) in THF (1 ml) containing 1,2-dibromoethane (146 μl, 1.53 mmol) was heated at 65° C. for 1 minute. The mixture was cooled to 25° C. and chlorotrimethylsilane (132 μl; 1.15 mmol) was added. Stirred at 20° C. for 15 minutes.

4-Chloro-2-(bromomethyl)phenyl phenylmethyl ether (3 g, 9.6 mmol) in THF was added dropwise to the above suspension of activated zinc dust. The solution was then transferred (using a round acrodisc to filter off the zinc) into a mixture of ethyl 6-bromo-2-pyridinecarboxylate (1.2 g, 5.3 mmol) and tetrakis(triphenylphosphine)palladium(0) (catalytic amount) in dry THF (15 ml) under nitrogen. The mixture was stirred at room temperature overnight. The resulting product (assume 0.0096 mol) and sodium methanethiolate (3.36 g, 5 equivalents) in DMF (~10 ml) was heated at 100° C. overnight. LC/MS—looked okay. Cooled down, quenched (diluted) with water and extracted with ethyl acetate (3×), dried over MgSO$_4$. Some compound crashed out when water was added. The organic phase residue and the solid residue were mixed together and used for the next step.

The product and 0.5 ml of H$_2$SO$_4$ were heated to reflux in ethanol (30 ml) overnight. LC/MS okay. Cooled down, vacuumed down, quenched (diluted) with water and extracted with ethyl acetate (3 times). The residue was purified by chromatography (Biotage, 25% ethyl acetate in isohexane) to give a white solid (1 g).

Rt=3.24, [MH+] 292, 294 [MH−] 290, 292.

Ethyl 5-[(5-chloro-2-hydroxyphenyl)methyl]-3-pyridinecarboxylate

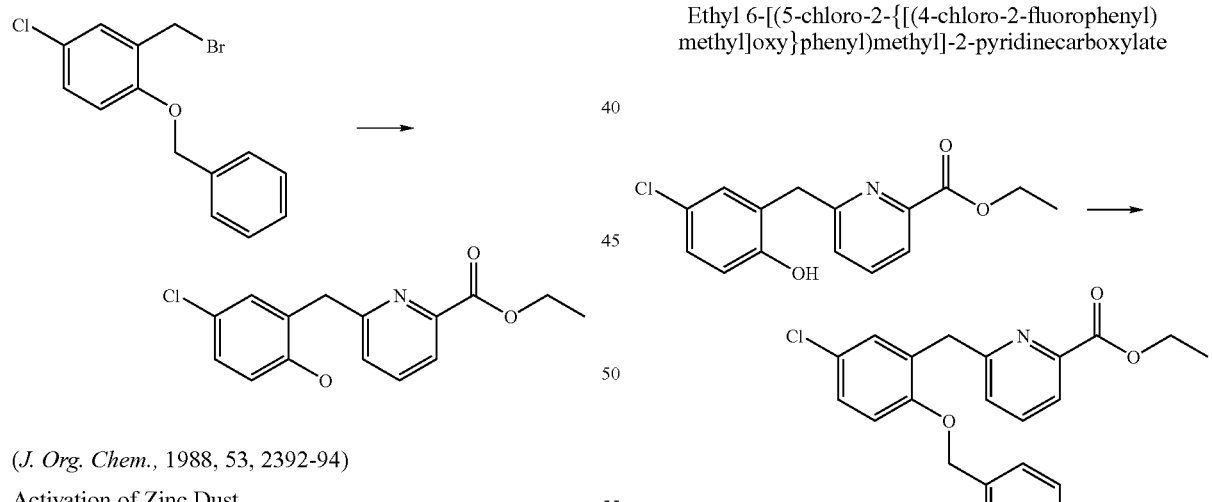

The title compound was prepared in a similar manner to ethyl 6-[(5-chloro-2-hydroxyphenyl)methyl]-2-pyridinecarboxylate using ethyl 5-bromo-3-pyridinecarboxylate instead of ethyl 6-bromo-2-pyridinecarboxylate. Rt=3.18 [MH+] 292, 294.

General Procedure 1

Ethyl 6-[(5-chloro-2-{[(4-chloro-2-fluorophenyl)methyl]oxy}phenyl)methyl]-2-pyridinecarboxylate A mixture of ethyl 6-[(5-chloro-2-hydroxyphenyl)methyl]-2-pyridinecarboxylate (92 mg, 0.31 mmol), potassium carbonate (109 mg, 2.5 equivalents) and 4-chloro-2-fluorobenzyl bromide (78 mg, 1.1 equivalents) in acetone (~6 ml) was heated at 50° C. for 3-4 hours until there was no more SM (starting material). Cooled down, filtered off and washed with acetone. LC/MS okay, Rt4.05. Purified by SPE, product came off with ~20% ethyl acetate in iso-hexane. 108 mg of a white solid. Rt=4.05 [MH+] 434, 437.

General Procedure 1A

To 100 mg of the appropriate phenol {ethyl 6-[(5-chloro-2-hydroxyphenyl)methyl]-2-pyridinecarboxylate) or ethyl 5-[(5-chloro-2-hydroxyphenyl)methyl]-3-pyridinecarboxylate} (0.34 mmol) in ~3 ml of acetone, 2.5 eq of $K_2CO_3$ (0.86 mmol 118 g) and 1.1 equivalents of the benzyl bromide (0.37 mmol) were added. The mixture was stirred at 60° C. for 4 hours. LC/MS—no starting material. Cooled down, filtered off the solid and vacuumed down. Purified by SPE (10 g, Flashmaster). Started with 5% of ethyl acetate in iso-hexane, the excess benzyl bromide came off. Then used 15-20% of ethyl acetate (in iso-hexane)—product came off. LC/MS obtained. Approximately 100 mg product obtained.

The following compounds were prepared by reacting the appropriate benzyl bromide with 6-[(5-chloro-2-hydroxyphenyl)methyl]-2-pyridinecarboxylate using similar methods to that described for General Procedure 1 or General procedure IA:

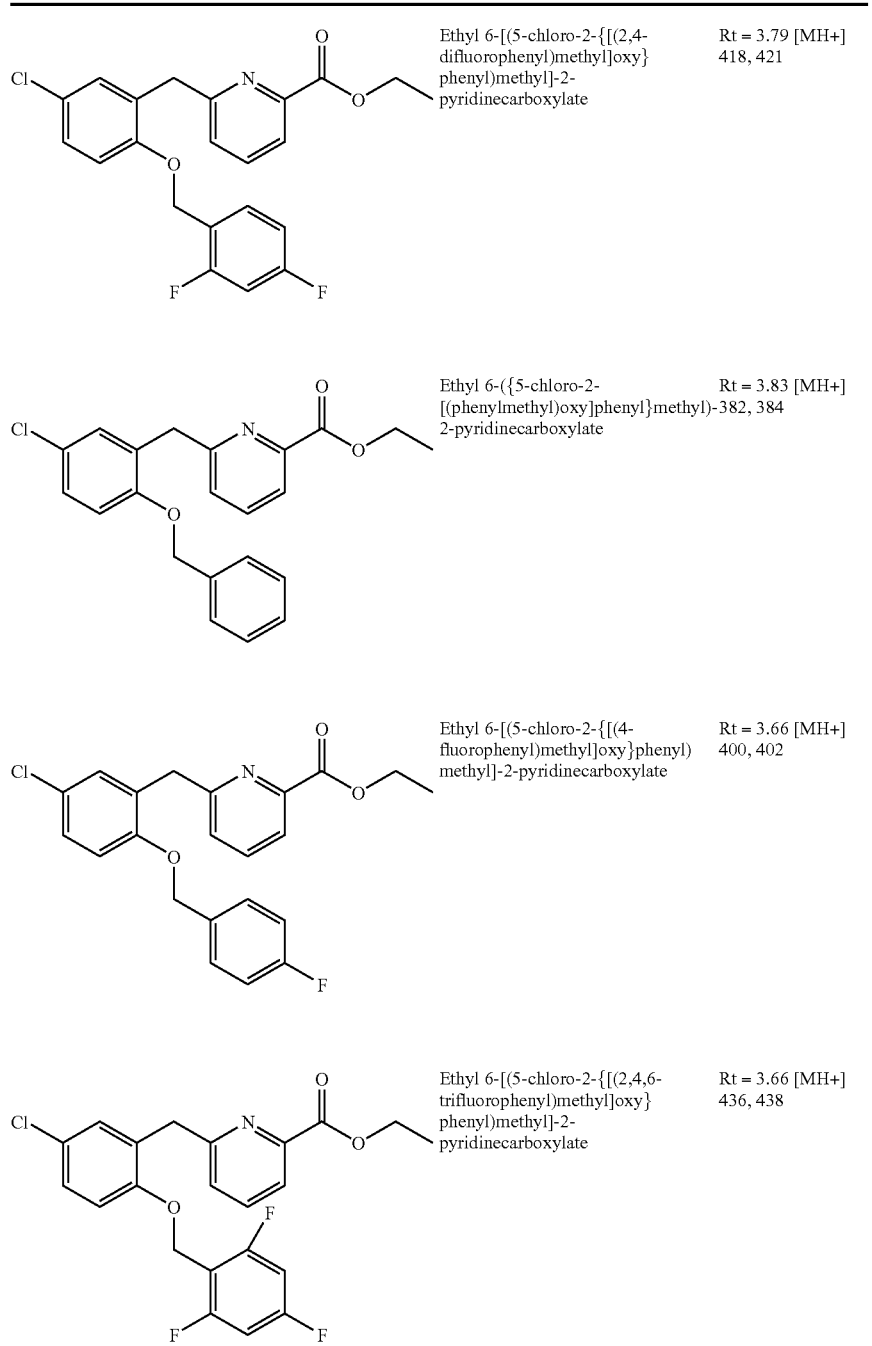

Ethyl 6-[(5-chloro-2-{[(2,4-difluorophenyl)methyl]oxy}phenyl)methyl]-2-pyridinecarboxylate  Rt = 3.79 [MH+] 418, 421

Ethyl 6-({5-chloro-2-[(phenylmethyl)oxy]phenyl}methyl)-2-pyridinecarboxylate  Rt = 3.83 [MH+] 382, 384

Ethyl 6-[(5-chloro-2-{[(4-fluorophenyl)methyl]oxy}phenyl)methyl]-2-pyridinecarboxylate  Rt = 3.66 [MH+] 400, 402

Ethyl 6-[(5-chloro-2-{[(2,4,6-trifluorophenyl)methyl]oxy}phenyl)methyl]-2-pyridinecarboxylate  Rt = 3.66 [MH+] 436, 438

| | | |
|---|---|---|
| 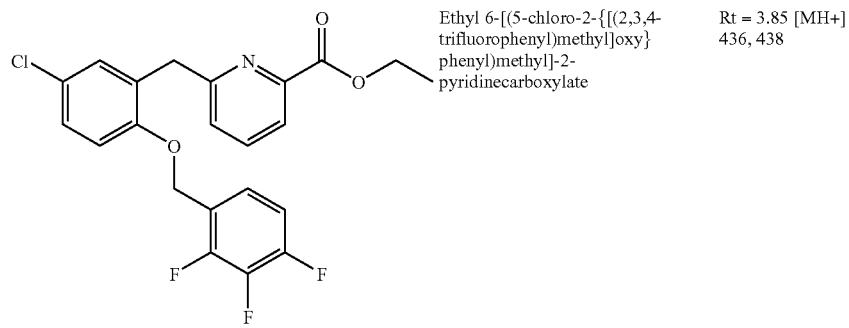 | Ethyl 6-[(5-chloro-2-{[(2,3,4-trifluorophenyl)methyl]oxy}phenyl)methyl]-2-pyridinecarboxylate | Rt = 3.85 [MH+] 436, 438 |
| 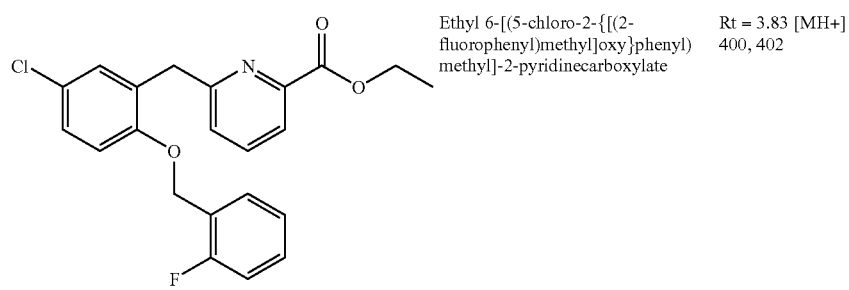 | Ethyl 6-[(5-chloro-2-{[(2-fluorophenyl)methyl]oxy}phenyl)methyl]-2-pyridinecarboxylate | Rt = 3.83 [MH+] 400, 402 |
| 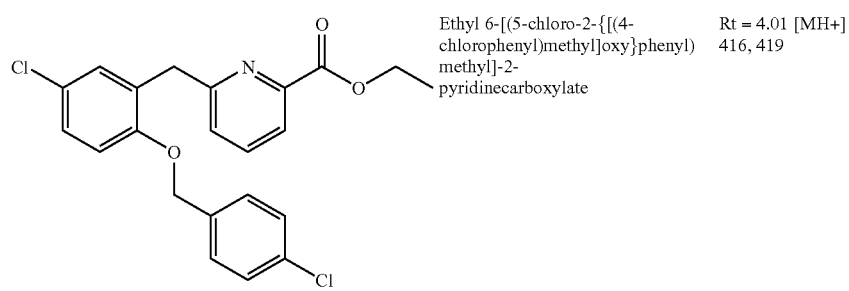 | Ethyl 6-[(5-chloro-2-{[(4-chlorophenyl)methyl]oxy}phenyl)methyl]-2-pyridinecarboxylate | Rt = 4.01 [MH+] 416, 419 |
| 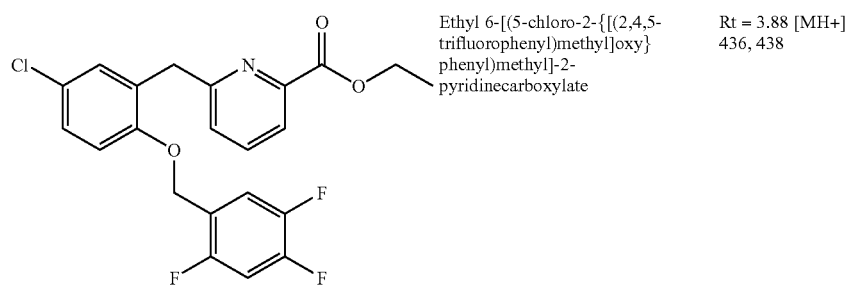 | Ethyl 6-[(5-chloro-2-{[(2,4,5-trifluorophenyl)methyl]oxy}phenyl)methyl]-2-pyridinecarboxylate | Rt = 3.88 [MH+] 436, 438 |
| 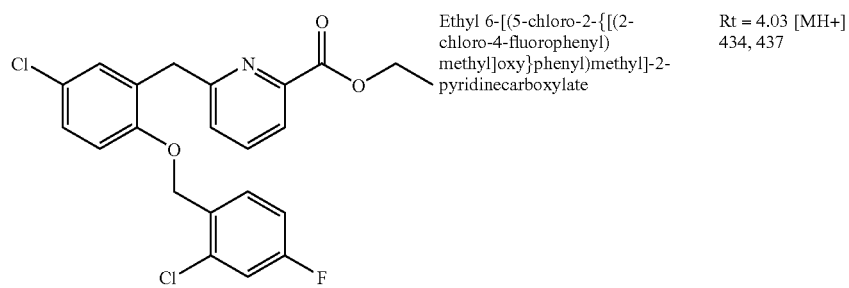 | Ethyl 6-[(5-chloro-2-{[(2-chloro-4-fluorophenyl)methyl]oxy}phenyl)methyl]-2-pyridinecarboxylate | Rt = 4.03 [MH+] 434, 437 |

-continued

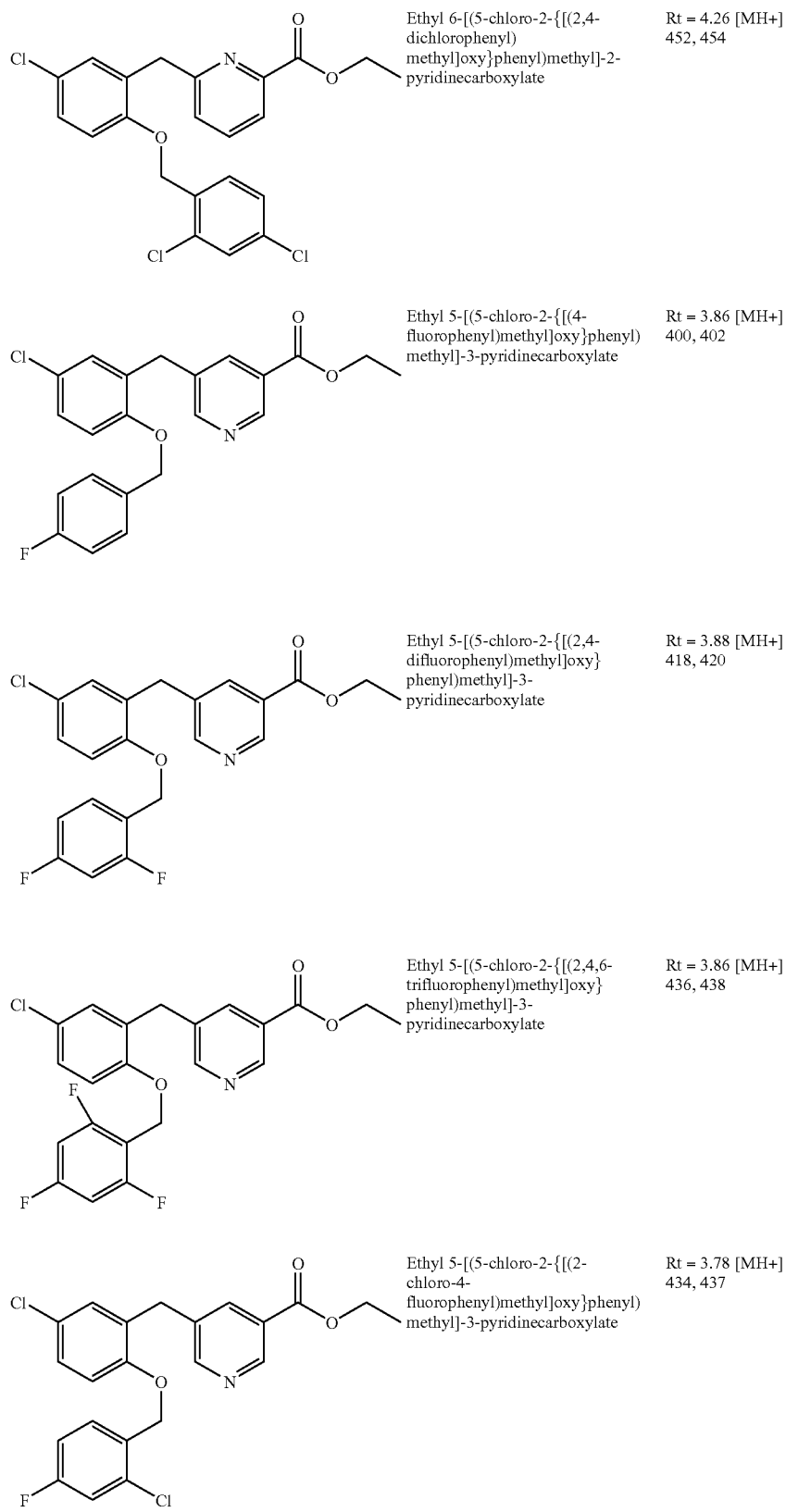

| | | |
|---|---|---|
| | Ethyl 6-[(5-chloro-2-{[(2,4-dichlorophenyl)methyl]oxy}phenyl)methyl]-2-pyridinecarboxylate | Rt = 4.26 [MH+] 452, 454 |
| | Ethyl 5-[(5-chloro-2-{[(4-fluorophenyl)methyl]oxy}phenyl)methyl]-3-pyridinecarboxylate | Rt = 3.86 [MH+] 400, 402 |
| | Ethyl 5-[(5-chloro-2-{[(2,4-difluorophenyl)methyl]oxy}phenyl)methyl]-3-pyridinecarboxylate | Rt = 3.88 [MH+] 418, 420 |
| | Ethyl 5-[(5-chloro-2-{[(2,4,6-trifluorophenyl)methyl]oxy}phenyl)methyl]-3-pyridinecarboxylate | Rt = 3.86 [MH+] 436, 438 |
| | Ethyl 5-[(5-chloro-2-{[(2-chloro-4-fluorophenyl)methyl]oxy}phenyl)methyl]-3-pyridinecarboxylate | Rt = 3.78 [MH+] 434, 437 |

| | | |
|---|---|---|
| 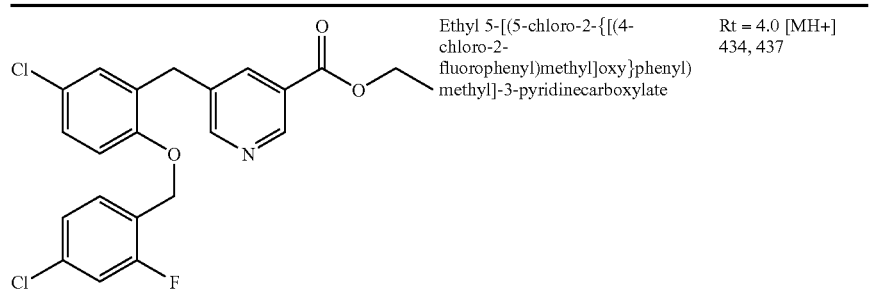 | Ethyl 5-[(5-chloro-2-{[(4-chloro-2-fluorophenyl)methyl]oxy}phenyl)methyl]-3-pyridinecarboxylate | Rt = 4.0 [MH+] 434, 437 |

Ethyl 6-[(5-chloro-2-{[(2-chlorophenyl)methyl]oxy}phenyl)methyl]-2-pyridinecarboxylate

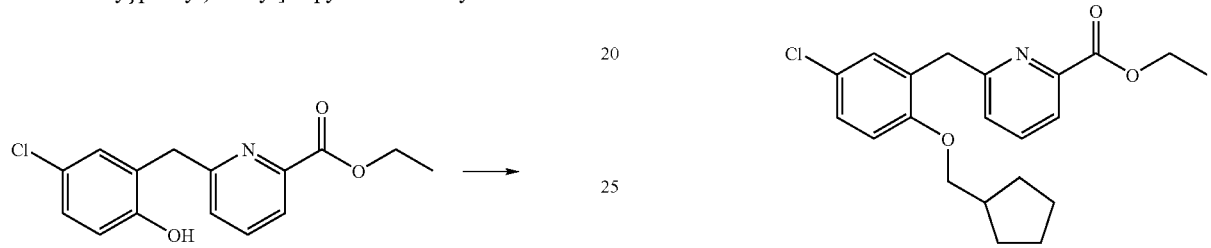

A solution of ethyl 6-[(5-chloro-2-hydroxyphenyl)methyl]-2-pyridinecarboxylate (60 mg, 0.21 mmol) in dry dimethylformamide (2.1 ml) was stirred at room temperature under an atmosphere of argon. Potassium carbonate (44 mg, 0.32 mmol) was added to the stirred solution. 2-Chlorobenzyl bromide (51 mg, 0.25 mmol) was added to the stirred solution. The solution was heated to 80° C. for ~17 hours (overnight). The reaction was worked up to yield the title compound.

Rt=3.61 [MH+] 416, 419.

Ethyl 6-({5-chloro-2-[(cyclopentylmethyl)oxy]phenyl}methyl)-2-pyridinecarboxylate

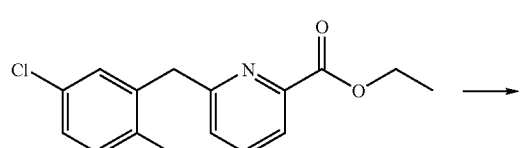

-continued

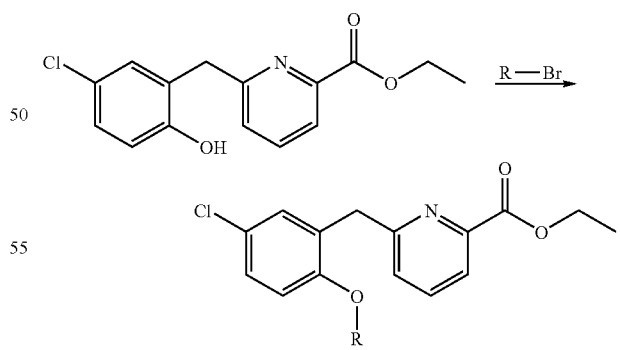

A mixture of ethyl 6-[(5-chloro-2-hydroxyphenyl)methyl]-2-pyridinecarboxylate (128 mg, 0.44 mmol), triphenylphosphine (115 mg, 0.44 mmol), diisopropylazodicarboxylate (86 µl, 0.44 mmol) and cyclopentanemethanol (43 µl, 0.4 mmol) in THF (5 ml) was stirred at room temperature for 6 hours. Further aliquots of triphenylphosphine (58 mg, 0.22 mmol), diisopropylazodicarboxylate (43 µl) and cyclopentanemethanol (22 µl, 0.2 mmol) were added and the reaction stirred for a further 18 hours. The solvent was removed in vacuum and the residue purified by flash chromatography using 15% ethyl acetate in isohexane to yield the title compound as a clear oil (164 mg). Rt=4.13 [MH+] 374, 376.

General Procedure 2

A solution of the phenol (0.060 g, 0.12 mol) in dry DMF (2.1 ml) was stirred at room temperature under an atmosphere of argon. Potassium carbonate (0.044 g, 0.32 mmol) was added to the stirred solution. The desired alkyl bromide (RBr, 0.25 mol) was added to the stirred solution. Solution heated to 80° C. for ~17 hours (overnight). The reaction was worked up and the residue was purified by flash chromatography on SiO₂, eluting with hexane containing a gradient of ethyl acetate (100-25%) to yield the product.

The following compounds were prepared by reacting the appropriate benzyl bromide, alkyl bromide or alkenyl bromide with 6-[(5-chloro-2-hydroxyphenyl)methyl]-2-pyridinecarboxylate using similar methods to that described for General Procedure 2 using 1.5 to 3 equivalents potassium carbonate:

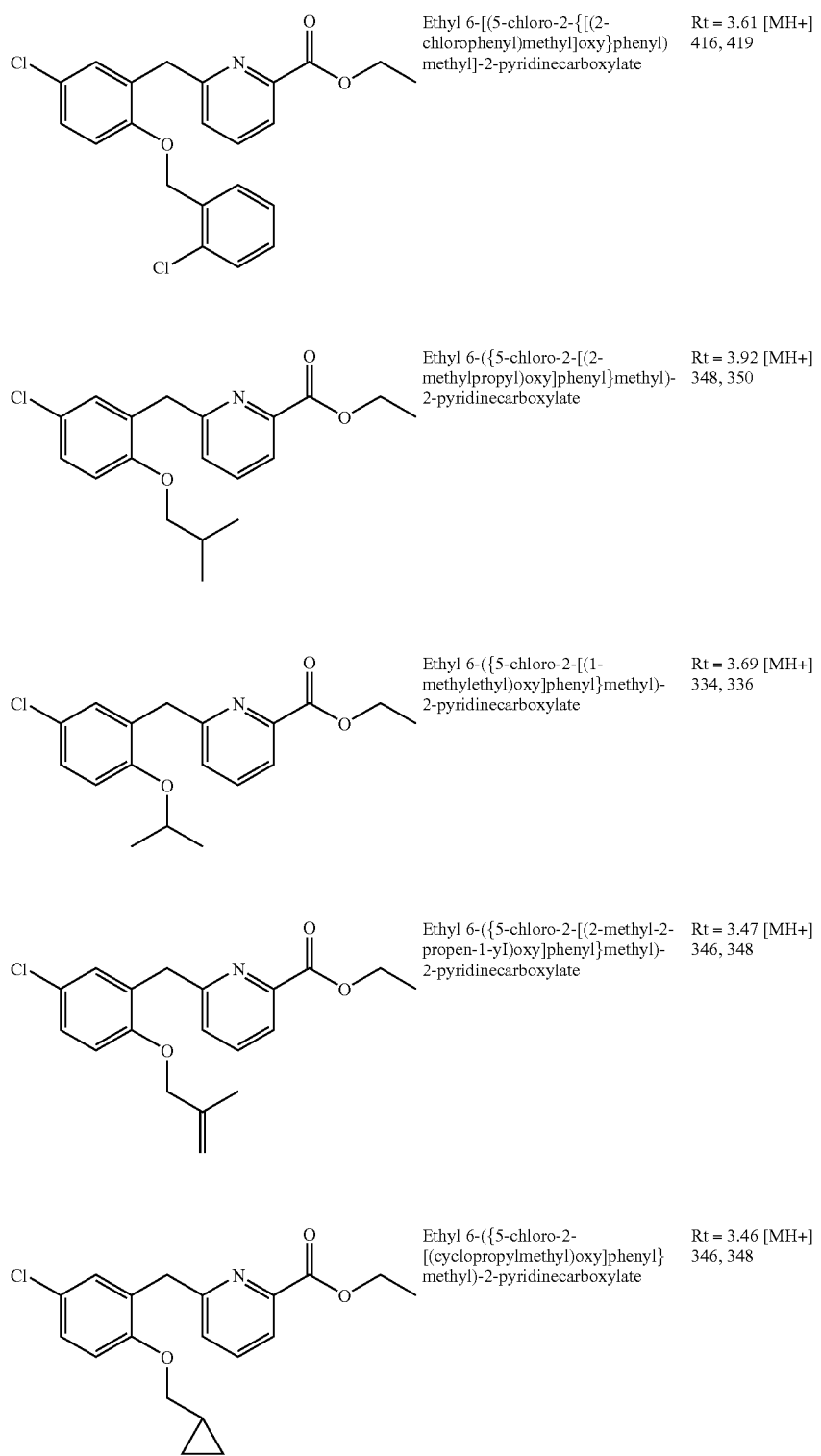

-continued

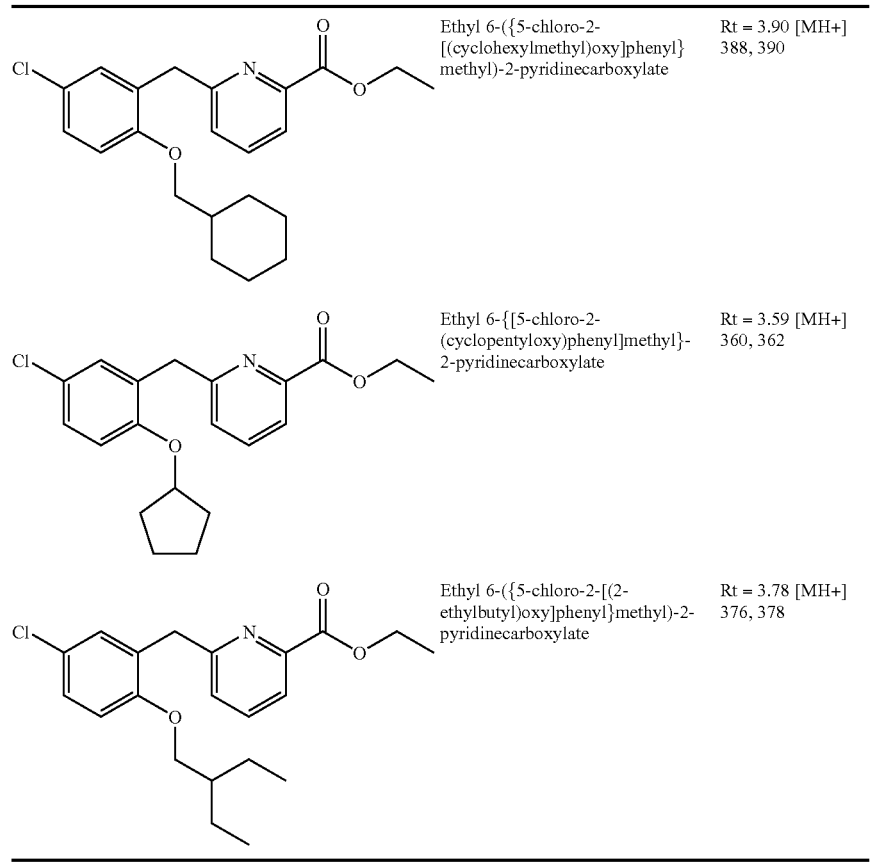

| Structure | Name | Rt / MH+ |
|---|---|---|
| (cyclohexylmethyl ether) | Ethyl 6-({5-chloro-2-[(cyclohexylmethyl)oxy]phenyl}methyl)-2-pyridinecarboxylate | Rt = 3.90 [MH+] 388, 390 |
| (cyclopentyloxy) | Ethyl 6-{[5-chloro-2-(cyclopentyloxy)phenyl]methyl}-2-pyridinecarboxylate | Rt = 3.59 [MH+] 360, 362 |
| (2-ethylbutyloxy) | Ethyl 6-({5-chloro-2-[(2-ethylbutyl)oxy]phenyl}methyl)-2-pyridinecarboxylate | Rt = 3.78 [MH+] 376, 378 |

Example 1

6-({5-Chloro-2-[(phenylmethyl)oxy]phenyl}methyl)-2-pyridinecarboxylic acid

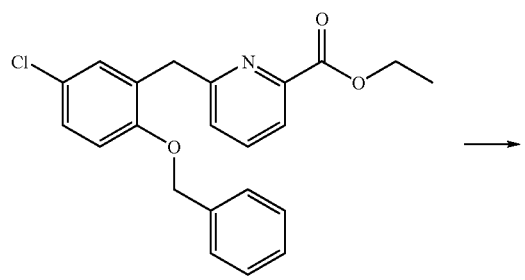

Ethyl 6-({5-chloro-2-[(phenylmethyl)oxy]phenyl}methyl)-2-pyridinecarboxylate (5.26 g, 13.8 mmol) was stirred at 60° C. for 2 hours in ethanol (15 ml) and 2M sodium hydroxide solution (5 mL). The reaction mixture was cooled and evaporated. The residue was diluted with water and extracted with diethyl ether. The aqueous phase was then acidified with glacial acetic acid and extracted with ethyl acetate (2×30 mL), dried (MgSO₄) and evaporated to give the title compound as a yellow oil (4.78 g).

$^1$H NMR (CDCl$_3$) δ: 4.19 (2H, s), 4.98 (2H, s), 6.87 (1H, d, J=9.2 Hz), 7.21-7.18 (4H, m), 7.32-7.33 (4H, m), 7.77 (1H, t, J=7.7 Hz), 8.04 (1H, d, J=7.6 Hz).

Example 2

6-({5-Chloro-2-[(2-methyl-2-propen-1-yl)oxy]phenyl}methyl)-2-pyridinecarboxylic acid

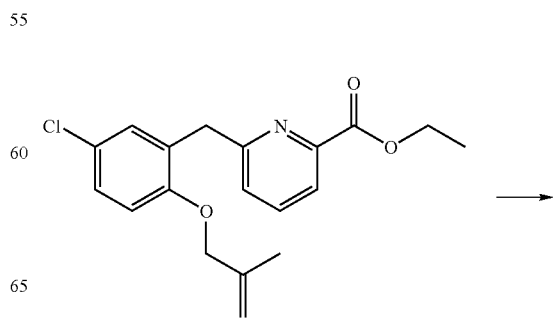

-continued

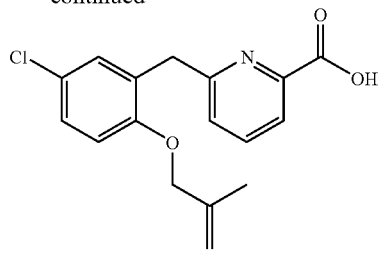

Ethyl 6-({5-chloro-2-[(2-methyl-2-propen-1-yl)oxy]phenyl}methyl)-2-pyridinecarboxylate (60 mg, 0.17 mmol) was stirred at 60° C. for 2 hours in ethanol (3 ml) and 2M sodium hydroxide solution (0.4 ml). The reaction mixture was cooled and evaporated. The residue was diluted with water and extracted with diethyl ether. The aqueous phase was then acidified with glacial acetic acid and extracted with ethyl acetate (2×20 ml), dried (MgSO$_4$) and evaporated to give the title compound as a yellow oil (38 mg).

$^1$H NMR (CDCl$_3$) δ: 1.67 (3H, s); 4.18 (2H, s); 4.34 (2H, s), 4.90 (1H, s), 4.92 (1H, s), 6.76 (1H, d J8.8 Hz), 7.15-7.17 (2H, m), 7.33 (1H, bs), 7.76 (1H, bs), 8.01 (1H, bs).

Example 3

Sodium 6-[(5-chloro-2-{[(4-chloro-2-fluorophenyl)methyl]oxy}phenyl)methyl]-2-pyridinecarboxylate

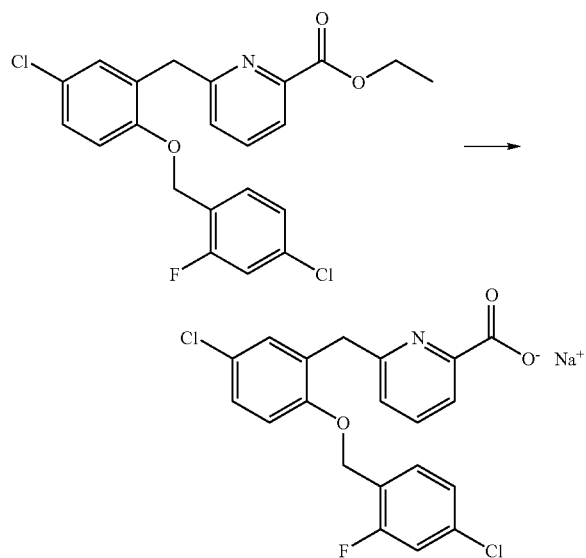

Ethyl 6-[(5-chloro-2-{[(4-chloro-2-fluorophenyl)methyl]oxy}phenyl)methyl]-2-pyridinecarboxylate (421.4 mg, 0.97 mmol) was suspended in ethanol (4 ml) and 2M sodium hydroxide (1 ml) and heated at 90° C. for 1.75 hours. Reaction complete after about 1 hour.

LC/MS: Rt=3.29 [ES+] 406, 408 [ES−] 404, 406

The white solid was diluted with water. The solid was collected by filtration and dried in a drying pistol overnight at 50° C. White solid collected (387.2 mg, 93%).

LC/MS: Rt=3.28 [ES+] 404, 406, 408.

$^1$H NMR (d$_6$ DMSO) δ: 4.09 (2H, s), 5.16 (2H, s), 6.92 (1H, dd, J=7.6, 1.1 Hz), 7.13 (1H, d, J=8.8 Hz), 7.21 (1H, d, J=2.7 Hz), 7.26 (1H, dd, J=8.7, 2.7 Hz), 7.32 (1H, dd, J=8.3, 2.2 Hz), 7.46 (1H, dd, J=10.0, 2.1 Hz), 7.49 (1H, dd, J=8.2, 8.2 Hz), 7.56 (1H, dd, J=7.6, 7.6 Hz), 7.67 (1H, dd, J=7.6, 1.1 Hz).

Sodium 6-[(5-chloro-2-{[(4-chloro-2-fluorophenyl)methyl]oxy}phenyl)methyl]-2-pyridinecarboxylate Alternative Route 1

Diethyl 2,6-pyridinedicarboxylate

A mixture of 95 g (0.569 mol) 2,6-pyridinedicarboxylic acid in 1 litre of ethanol was stirred while 50 ml of sulphuric acid was added carefully. The resulting suspension was heated at 90° C., all going into solution after ~10 minutes. Refluxed for 4 hours, about 80% gone but not changing so a further 10 ml of sulfuric acid was added and refluxed overnight—no change. Cooled, evaporated and dissolved in ether/water/ice and 200 ml of concentrated aqueous ammonia was added. The organic phase was dried and evaporated to give 82.6 g of white solid.

Ethyl 6-(hydroxymethyl)-2-pyridinecarboxylate

Reaction 1

2.28 g (60 mmol) of sodium borohydride were added to a stirred solution of 22.3 g (100 mmols) of diethyl 2,6-pyridinedicarboxylate in 200 ml of ethanol and stirred for 4 hours then a further 570 mg (15 mmols) of sodium borohydride was added and stirred for 15 hours. Evaporated, dissolved in 200 ml of dichloromethane and washed with 50 ml water. Aqueous layer extracted three times with dichloromethane and the combined organics washed with brine. Dried, evaporated, triturated with ether and filtered off to give 13.01 g of white solid.

Reaction 2

11.4 g (0.3 mol) of sodium borohydride was added in one portion to a stirred solution of 111.5 g (0.5 mol) of diethyl 2,6-pyridinedicarboxylate in 1 litre of ethanol and stirred for 6 hours when a further 2.85 g (0.075 mol) of sodium borohydride were added and the mixture stirred overnight before being evaporated. The residue was dissolved in 800 ml dichloromethane and washed with water. The aqueous was extracted with 4×50 ml of dichloromethane. The combined organics were dried, evaporated and combined with the product from reaction 1 (13.1 g). The combined material was washed through a pad of silica on a large sinter with ethyl acetate (2 litres) which was evaporated and triturated with ether and filtered off to give 72.6 g of a white solid. The MLS (mother liquors) were evaporated and biotaged (chromatographed) [ethyl acetate/hexane (3:1)] to give a further 2.9 g of product.

Ethyl 6-(chloromethyl)-2-pyridinecarboxylate hydrochloride

Reaction 1

28.56 g (0.24 mol) of thionyl chloride were added over 5 minutes to a stirred solution of 36.2 g (0.2 mol) of ethyl 6-(hydroxymethyl)-2-pyridinecarboxylate in dichloromethane (250 ml) with water bath cooling and stirred for 30 minutes. Evaporated in vacuo, and re-evaporated with 100 ml toluene to give 48 g of white oil, which was used immediately.

Reaction 2

As for Reaction 1, using 45.14 g of ethyl 6-(hydroxymethyl)-2-pyridinecarboxylate and 33 g thionyl chloride in 500 ml dichloromethane. Yield 59.9 g 4-Chloro-2-iodophenol 109.4 g (0.436 mol) of boron tribromide were added over 10 minutes to a stirred solution of 90 g (0.335 mol) of 4-chloro-2-iodoanisole in dichloromethane (900 ml) at −78° C. under nitrogen. Cooling was removed and allowed to warm to room temperature and stirred for 5 hours. Poured onto ice and diluted with a further 800 ml of water. The organic phase was separated, the aqueous extracted with dichloromethane and the combined organics washed with saturated sodium bicarbonate, dried and evaporated to give 84.87 g of off-white solid.

4-Chloro-1-{[(4-chloro-2-fluorophenyl)methyl]oxy}-2-iodobenzene

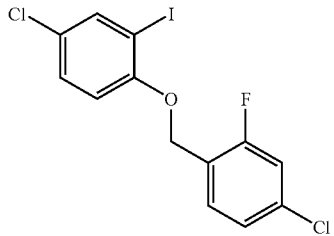

Reaction 1

A mixture of 53.5 g (0.21 mol) of 4-chloro-2-iodophenol, 55.2 g (0.4 mol) of potassium carbonate and 48 g (0.215 mol) of 4-chloro-2-fluorobenzyl bromide in acetone (500 ml) was stirred and refluxed for 2 hours. Cooled, filtered and evaporated and triturated with hexane (500 ml) at −10° C. and the solid filtered off. The MLS (mother liquors) were evaporated in vacuo and re-triturated with hexane (75 ml) at −10° C. and the solid filtered off to give a further 3.1 g of product. Total yield of 81.5 g.

Reaction 2

As for Reaction 1, using 84.87 g 4-chloro-2-iodophenol, 76 g 4-chloro-2-fluorobenzyl bromide and 92 g potassium carbonate in 900 ml acetone. Yield 129.36 g. Identical by TLC with product of Reaction 1.

(5-Chloro-2-{[(4-chloro-2-fluorophenyl)methyl]oxy}phenyl)boronic acid

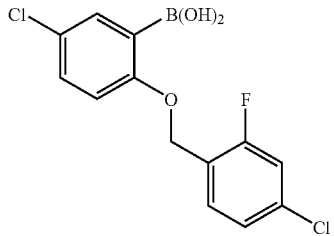

Reaction 1

250 ml (0.5 mol) of 2M isopropylmagnesium chloride was added dropwise over 30 minutes to a stirred solution of 99.25 g (0.25 mol) of 4-chloro-1-{[(4-chloro-2-fluorophenyl)methyl]oxy}-2-iodobenzene in dry THF (1 litre) under argon at −40° C. Stirred for one hour at −40° C. then 52 g (0.5 mol) of trimethyl borate added over 20 minutes at −40° C., cooling was removed and the mixture allowed to warm to room temperature. 2M hydrochloric acid (500 ml) was added with vigorous stirring, temperature rose to ~30° C. Organic phase was separated, washed with brine, dried, evaporated, triturated with ether, and the solid filtered off. The MLS (mother liquors) were evaporated, triturated with ether, and the solid filtered off, MLS evaporated, triturated with ether and the solid filtered off again. Three batches obtained: $1^{st}$ 45 g, $2^{nd}$ 19 g, $3^{rd}$ 7 g. All identical by TLC. Total yield of 71 g.

Reaction 2

As for reaction 1, using 90.5 g 4-chloro-1-{[(4-chloro-2-fluorophenyl)methyl]oxy}-2-iodobenzene, 228 ml isopropylmagnesium chloride and 47.42 g trimethyl borate. Yield 66.8 g. NMR showed trace impurities. LCMS OK.

Ethyl 6-[(5-chloro-2-{[(4-chloro-2-fluorophenyl)methyl]oxy}phenyl)methyl]-2-pyridinecarboxylate A mixture of 78.56 g (249.4 mmol) of (5-chloro-2-{[(4-chloro-2-fluorophenyl)methyl]oxy}phenyl)boronic acid, 59.9 g (249.4 mol) of ethyl 6-(chloromethyl)-2-pyridinecarboxylate hydrochloride, 137.68 g (997.7 mol) of potassium carbonate and 28.89 g (24.95 mmol) of tetrakis(triphenylphoshine)palladium(0) in 1:1 toluene/ethanol (1840 ml) was stirred and heated at 90° C. under argon for 2 hours. Cooled, diluted with water/ether and filtered. Organic phase was washed with 2M hydrochloric acid and water, dried overnight (sodium sulphate), filtered and evaporated. Dissolved in dichloromethane, filtered to remove some insoluble material and the filtrate applied to a large column on the Biotage 75 and eluted with 15% ethyl acetate in hexane. Some purification but lower spot started to elute with product so eluent changed to ethyl acetate/hexane (1:1) and all fractions containing product combined and evaporated. Redissolved in dichloromethane and biotaged (chromatographed) again on same size column eluting with 4 litres of (3:1) dichloromethane/hexane changing to 5% ethanol in dichloromethane to remove the remaining product. Evaporated in vacuo and recrystallised from ethanol (1 litre) cooling to 20° C. in an ice bath then filtering off immediately to give 46 g of product. MLS (mother liquors) were left over the weekend when more solid separated which was filtered off but TLC showed this to be impurity and leaving very of this in the filtrate. MLS evaporated and recrystallised from ethanol (140 ml) to give 9.4 g of product. NMR and LC/MS of both products identical. (total yield of 55.4 g).

Sodium 6-[(5-chloro-2-{[(4-chloro-2-fluorophenyl)methyl]oxy}phenyl)methyl]-2-pyridinecarboxylate

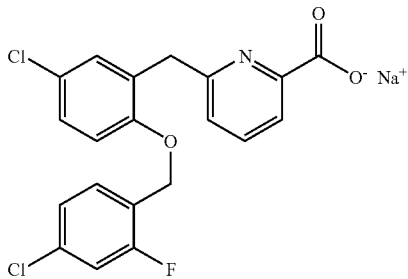

117 g (0.27 mol) of ethyl 6-[(5-chloro-2-{[(4-chloro-2-fluorophenyl)methyl]oxy}phenyl)-methyl]-2-pyridinecarboxylate were dissolved in ethanol (1 litre) (heating required) and 2M sodium hydroxide (200 ml) was added while still hot. Left to crystallise, and when at room temperature was diluted with an equal volume of water. After one hour at room temperature the solid was filtered off and washed with ethanol/water (1:3). MLS (mother liquors) were evaporated to remove ethanol, the solid was filtered off and the two lots were combined and washed with water and ether. Dried in a vacuum oven for 16 hours at 40° C. and 3 days at 60° C. Yield 110.5 g.

$^1$H NMR (d-6 DMSO) δ: 4.14 (2H, s), 5.16 (2H, s), 6.94 (1H, dd, J=7.7, 1.1 Hz), 7.14 (1H, d, J=8.8 Hz), 7.22 (1H, d, J=2.7 Hz), 7.26 (1H, dd, J=8.7, 2.7 Hz), 7.29 (1H, dd, J=8.3, 2.0 Hz), 7.46 (1H, dd, J=10.1, 1.9 Hz), 7.47 (1H, m), 7.59 (1H, dd, J=7.7, 7.7 Hz), 7.76 (1H, dd, J=7.7, 1.1 Hz).

$^{13}$C NMR (d-6 DMSO) δ: 167.9, 159.8 (d, 249.9 Hz), 158.2, 157.3, 154.3, 136.6, 133.5 (d, 10.5 Hz), 131.3 (d, 5.0 Hz), 130.7, 130.1, 127.1, 124.8 (d, 3.4 Hz), 124.6, 122.8 (d, 14.6 Hz), 122.3, 121.1, 115.9 (d, 24.9 Hz), 113.9, 63.3 (d, 3.1 Hz), 37.5.

6-[(5-chloro-2-{[(4-chloro-2-fluorophenyl)methyl]oxy}phenyl)methyl]-2-pyridinecarboxylic acid Sodium 6-[(5-chloro-2-{[(4-chloro-2-fluorophenyl)methyl]oxy}phenyl)methyl]-2-pyridinecarboxylate (3.0 g) was suspended in ethyl acetate (100 ml) and water (100 ml) with stirring. Acetic acid (1.0 ml) was added to give two clear phases which were separated. The ethyl acetate layer was dried over magnesium sulfate and concentrated to give an oil which crystallised after a few minutes. Toluene (100 ml) was added and the solution was re-evaporated to give a white solid. Left at 20 mBar for 5 hours at 45° C. 2.69 g.

$^1$H NMR (Bruker AV400) (CD$_3$OD) δ: 4.21 (2H, s); 5.03 (2H, s); 7.04 (1H, d J=8.7 Hz); 7.12-7.19 (2H, m); 7.22-7.29 (3H, m); 7.29-7.34 (1H, m); 7.80 (1H, t, J=7.7 Hz); 7.95 (1H, d, J=7.7 Hz).

Sodium 6-[(5-chloro-2-{[(4-chloro-2-fluorophenyl)methyl]oxy}phenyl)methyl]-2-pyridinecarboxylate

Alternative Route 2

4-Chloro-2-iodophenol

Boron tribromide (1349 g) was added to a solution of 4-chloro-2-iodoanisole (1025 g) in dichloromethane (10.3 L) under nitrogen at such a rate that the temperature remained at 0-5° C. The solution was then warmed to 20° C. and stirred for c. 19 h until the reaction was complete by HPLC. This organic solution was added to water (8.2 L) and the mixture was cooled to 5° C. to 10° C. DCM (770 ml) was added and the resulting biphasic mixture was then stirred at 5° C. for 15 min before being warmed to 22° C. and then finally stirred at 22° C. for 20 min before separating the phases. The separated organic phase was washed with aqueous saturated sodium bicarbonate (3.1 L), water (3.1 L) and then evaporated on a Buchi to give the title compound. (963.6 g)

Ethyl 6-(chloromethyl)-2-pyridinecarboxylate

Thionyl chloride (13.8 ml) was added over ~15 minutes to a stirred solution of ethyl 6-(hydroxymethyl)-2-pyridinecarboxylate (28.5 g) in MDC (200 ml) maintaining the temperature at 10-15° C. using an ice-water bath. On completion of the addition the mixture was stirred at room temperature for 1 hour. The solvent was evaporated and the residue partitioned between toluene (200 ml)/saturated bicarb (sodium bicarbonate solution, 200 ml). The layers were separated and the organic phase washed with water (150 ml). The solvent was evaporated to leave a pale oil which solidified on standing. (31.3 g).

4-Chloro-1-{[(4-chloro-2-fluorophenyl)methyl]oxy}-2-iodobenzene

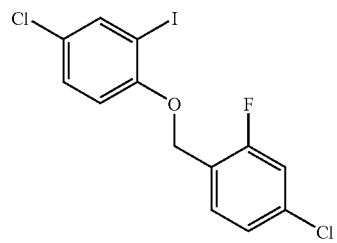

To a solution of 4-chloro-2-iodophenol (899 g, 1 eq) and 4-chloro-2-fluorobenzyl bromide (700 g, 1.02 eq) in acetone (8.1 L) was added anhydrous potassium carbonate (926 g). The stirred suspension was then heated to reflux for 30 minutes. 0.12% starting material was observed by HPLC. The product mixture was cooled to 20-25° C. HPLC showed complete consumption of starting material. Inorganic material was then removed by filtration. The residue was washed with acetone (3.6 L) and the combined filtrate and washes were concentrated to 5 vol by atmospheric distillation. Isooctane (4.5 L) was added and reconcentrated to 5 vol by atmospheric distillation. This was repeated once more. The solution was then cooled from 85° C. to 75° C. No precipitation occurred. The batch was then cooled further to 55° C. over 30 minutes, leading to the formation of an immobile suspension. The batch was re-heated to 65° C. which thinned the suspension. The batch was then cooled to 55° C. over 30 minutes. This caused a more controlled precipitation with a mobile suspension.

The batch was then cooled to 20° C. over 30 min. This led to a skin of product forming on all surfaces of the vessel whilst the suspension stayed mobile. The mixture was then stirred overnight at 20° C. The mixture was then cooled to −5° C. over 30 minutes and aged at −5° C. for 1.5 h. A crust formed on the bottom of the vessel. The mother liquors were recycled 4 times to remove this material. When the crust was dislodged, this wedged against the stirrer causing it to break at the top of the guide. The final recycle of mother liquors removed this from the vessel, following manual breaking with a long spatula. The solid was then collected by filtration. The filter cake was washed with iso-octane (1.5 L) chilled to −5° C. The solid was then dried in vacuo at 45° C. to a constant weight. Yield 1312.4 g 2-(5-chloro-2-{[(4-chloro-2-fluorophenyl)methyl]oxy}phenyl)-4,4,5,5-tetramethyl-1,3,2-dioxaborolane

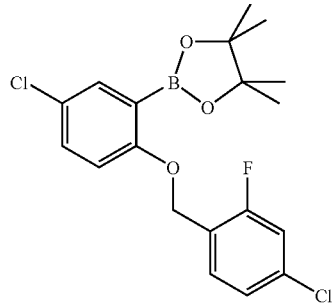

Reaction 1

4-Chloro-1-{[(4-chloro-2-fluorophenyl)methyl]oxy}-2-iodobenzene (18.8 g) was dissolved in dry THF (188 ml) under $N_2$ and the solution cooled to −10° C. in a cardice (dry ice)/acetone bath. To the cooled solution was added isopropyl magnesium chloride (47 ml of 2M solution in diethyl ether) dropwise over 23 minutes maintaining the reaction temperature at −10° C. (max temp over addition −9° C., Min temp over addition −12° C.). After the addition was completed the residual chloride (isopropyl magnesium chloride) was washed into the reaction with dry THF (5 ml). The reaction mixture was stirred at −10° C. for 15 minutes then isopropyl tetramethyl dioxaborolane (23 ml) was added in one portion. Reaction exotherm (−10° C. to 5° C.). The cooling bath was removed and the reaction mixture allowed to warm to ambient temperature. The reaction was stirred at ambient temperature overnight under static $N_2$ flow.

The cloudy reaction mixture was quenched by the addition of 50% saturated ammonium chloride solution (188 ml) and the mixture stirred then separated. The aqueous phase was re-extracted with THF (50 ml). The bulked organic phases were washed with water (190 ml). Emulsion formed. Solid NaCl added to break emulsion, required heating with airgun to finish separation. The THF solution (still slightly cloudy) was evaporated under reduced pressure at 40° C. to leave a wet solid. Isopropyl alcohol (50 ml) was added and re-stripped to leave a white solid. Isopropyl alcohol (20 ml) was added and the white slurry cooled in an ice-bath for 30 minutes. Solid was filtered, washed with the mother liquor, then washed on the pad with IPA (10 ml, cold) and sucked dry on the pad. The solid was transferred to a dish and dried in a vacuum oven at 50° C. over weekend to give the title product (16.77 g). NMR showed clean product.

Reaction 2

A solution of 4-chloro-1-{[(4-chloro-2-fluorophenyl)methyl]oxy}-2-iodobenzene (20 g, 50 mmol) in dry THF (200 ml) was cooled to −10° C. Isopropyl magnesium chloride (2M in THF, 50 ml, 100 mmol) was added dropwise over ~15 mins, then the mixture was stirred at −10° C. for 15 mins. 2-Isopropoxy-4,4,5,5-tetramethyl-1,3,3-borolane (24.4 ml, 120 mmol) was added and the mixture was allowed to warm to room temperature and stirred for 18 h. TMBE (200 ml) and saturated $NH_4Cl$ (200 ml) were added, and the layers separated. The organic phase was dried over $MgSO_4$ and evaporated to a white semi-solid. Trituration with isohexane (50 ml) gave a white solid. The solid was filtered off, washed with isohexane (20 ml) and dried in a vacuum oven at 50° C. for 18 h to give the title compound (16.2 g).

Reaction 3

A solution of 4-chloro-1-{[(4-chloro-2-fluorophenyl)methyl]oxy}-2-iodobenzene (20 g, 50 mmol) in dry THF (200 ml) was cooled to −10° C. Isopropyl magnesium chloride (2M in diethyl ether, 50 ml, 100 mmol) was added dropwise over ~15 mins, then the mixture was stirred at −10° C. for 15 mins. 2-Isopropoxy-4,4,5,5-tetramethyl-1,3,3-borolane (24.4 ml, 120 mmol) was added and the mixture was allowed to warm to room temperature and stirred for 18 h. TMBE (200 ml) and saturated $NH_4Cl$ (200 ml) were added, and the layers separated. The organic phase was washed with water (200 ml), dried over $MgSO_4$ and evaporated to a white semi-solid. Trituration with isohexane (50 ml) gave a white solid which was filtered, washed with isohexane (20 ml) and dried in a vacuum oven at 50° C. for 18 h to give the title compound (16.4 g).

Ethyl 6-[(5-chloro-2-{[(4-chloro-2-fluorophenyl)methyl]oxy}phenyl)methyl]-2-pyridinecarboxylate

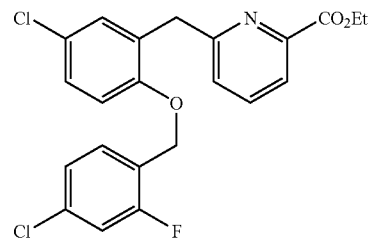

Reaction 1

A mixture of 2-(5-chloro-2-{[(4-chloro-2-fluorophenyl)methyl]oxy}phenyl)-4,4,5,5-tetramethyl-1,3,2-dioxaborolane (8 g), ethyl 6-(chloromethyl)-2-pyridinecarboxylate (4 g), $K_2CO_3$ (5.6 g) and (tetrakis(triphenylphoshine)palladium (0) (1.2 g) in toluene (75 ml) and ethanol (5 ml) was stirred and heated at 80-90° C. for 4 hours. Complete consumption of SM (starting material), formation of product and some homo-coupled product. The mixture was cooled to room temperature, water (100 ml) was added and the mixture stirred vigorously for 5 minutes. A clear two phase mixture was formed. The layers were separated and the aqueous phase washed with water (100 ml). The solvent was evaporated to leave a yellow-brown solid (11 g).

A further batch of crude product was prepared by as follows. A mixture of 2-(5-chloro-2-{[(4-chloro-2-fluorophenyl)methyl]oxy}phenyl)-4,4,5,5-tetramethyl-1,3,2-dioxaborolane (16 g), ethyl 6-(chloromethyl)-2-pyridinecarboxylate (8 g), $K_2CO_3$ (11.2 g) and $Pd(PPh)_4$ (tetrakis(triphenylphoshine)palladium(0), 2.4 g) in toluene (150 ml) and ethanol (10 ml) was stirred and heated at 80-90° C. for 6 hours. HPLC showed complete consumption of SM (starting material), formation of product and some homo-coupled material. The mixture was cooled to room temperature, water (150 ml) was added and the mixture stirred vigorously for 5 minutes. A clear two phase mixture was formed. The layers were separated and the aqueous phase washed with water (150 ml). The solvent was evaporated to leave a yellow-brown solid (22 g).

The two batches were combined and dissolved in MDC (dichloromethane, 200 ml). The solution was filtered to remove a small amount of insoluble material. The solution was evaporated and the residue recrystallised from ethanol (170 ml) with hot filtration. The solution was cooled to room temperature for 2 hours, then 0-5° C. for 2 hours, then the solid product was filtered off, washed with ethanol (25 ml) and dried in a vacuum oven for 18 hours at 45° C. to give the title compound (21.2 g). HPLC showed some impurities.

Reaction 2

Toluene (55 ml) and ethanol (55 ml) were added to a mixture of 2-(5-chloro-2-{[(4-chloro-2-fluorophenyl)methyl]oxy}phenyl)-4,4,5,5-tetramethyl-1,3,2-dioxaborolane (11 g, 27 mol), ethyl 6-(chloromethyl)-2-pyridinecarboxylate (5.5 g, 27 mol), $K_2CO_3$ (7.7 g, 54 mol) and (tetrakis(triphenylphoshine)palladium(0), (1.65 g, 5 mol %) and the mixture was heated at 80-90° C. for 1 hour. Additional toluene (55 ml) was added and the mixture was cooled to room temperature. Water (100 ml) was added and the mixture was stirred vigorously for 5 minutes. The layers were separated and the organic phase was washed with water. The solvent was evaporated to leave a brown semi-solid. The crude material was re-crystallised from ethanol (75 ml) with hot filtration. The filtrate was cooled to 0.5° C. for 2 hours. The product was filtered, washed with ethanol and dried in a vacuum oven at 50° C. overnight. A 7 g sample was purified by chromatography on silica gel (70 g), eluting with MDC (100 ml fractions taken). Fractions 2-14 were combined and evaporated to give a white solid, which was recrystallised from ethanol (25 ml).

Sodium 6-[(5-chloro-2-{[(4-chloro-2-fluorophenyl)methyl]oxy}phenyl)methyl]-2-pyridinecarboxylate

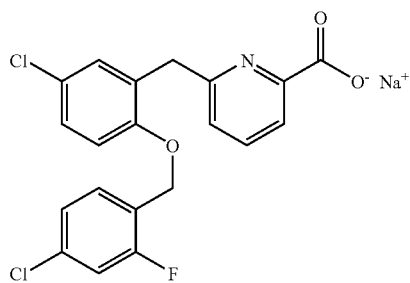

Ethyl 6-[(5-chloro-2-{[(4-chloro-2-fluorophenyl)methyl]oxy}phenyl)methyl]-2-pyridinecarboxylate (2 g) was dissolved in ethanol (15 ml) at reflux. 2M Sodium hydroxide (3.4 ml) was added and the solution heated under reflux for 30 minutes. No residual starting material by HPLC. The solution was filtered and the filter washed with a mixture of hot ethanol (5 ml) and water (5 ml). The combined filtrate and wash were re-heated to reflux, and water (15 ml) added dropwise over ~5 minutes and the clear solution allowed to cool slowly to room temperature. The product crystallised rapidly at ~35° C. The resulting thick suspension was cooled to 20-25° C. and stirred for 1 hour. The product was isolated and washed with 1:3 ethanol:water (20 ml) and then dried overnight at 50° C. in vacuo to give the title compound (1.94 g).

6-[(5-chloro-2-{[(4-chloro-2-fluorophenyl)methyl]oxy}phenyl)methyl]-2-pyridinecarboxylic acid, tris (hydroxymethyl)aminomethane salt 6-[(5-chloro-2-{[(4-chloro-2-fluorophenyl)methyl]oxy}phenyl)methyl]-2-pyridinecarboxylic acid (300 mg) was dissolved in methanol (5 ml) at 60° C. Tris(hydroxymethyl)aminomethane (TRIS, 89.5 mg) did not dissolve in MeOH (1 ml) at RT (room temperature). The TRIS suspension was added to the 6-[(5-chloro-2-{[(4-chloro-2-fluorophenyl)methyl]oxy}-phenyl)methyl]-2-pyridinecarboxylic acid solution in one go, washing with the reaction mixture. Immediately after the addition, solid precipitated and set solid. Methanol (9 ml) was added to mobilise the suspension. The suspension was left to temperature cycle at 0-40° C. over the weekend. Analysis of the suspension by polarised light microscopy showed birefringent material. The solid was isolated by filtration and dried in vacuo at 40° C. overnight giving a white solid (281.6 mg). NMR consistent with a 1:1 salt.

$^1$H NMR (Bruker DPX400) (DMSO-$d_6$) δ: 3.48 (6H, s); 4.07 (2H, s); 5.13 (2H, s); 7.01 (1H, d of d, J=7.6, 0.8 Hz); 7.13 (1H, d, J=8.7 Hz); 7.24-7.32 (3H, m); 7.42-7.50 (2H, m); 7.63 (1H, t, J=7.7 Hz); 7.69 (1H, dd, J=7.6, 0.8 Hz).

6-[(5-chloro-2-{[(4-chloro-2-fluorophenyl)methyl]oxy}phenyl)methyl]-2-pyridinecarboxylic acid, methanesulfonic acid salt 6-[(5-chloro-2-{[(4-chloro-2-fluorophenyl)methyl]oxy}phenyl)methyl]-2-pyridinecarboxylic acid (300 mg, 0.738 mmol) was dissolved in MIBK (methyl isobutyl ketone, 2.4 ml) at 80° C. Methane sulfonic acid (12 µl from a total of 47.9 µl) was added at 80° C. Solid precipitated and the reaction mixture set solid. Extra MIBK (2.6 ml) was added to mobilise the suspension. The remaining methane sulfonic acid (35.9 µl) was added and the suspension was stirred at 80° C. The suspension was left to temperature cycle over the weekend at 0-40° C. Analysis of the suspension by polarised light microscopy showed birefringent material. The solid was isolated by filtration, washed with MIBK and dried in vacuo overnight at 40° C. giving a white solid (226.7 mg).

$^1$H NMR (Bruker DPX400) (DMSO-$d_6$) δ: 2.34 (3H, s); 4.15 (2H, s); 5.10 (2H, s); 7.14 (1H, d, J=8.8 Hz); 7.25 (1H, dd, J=8.3, 1.9 Hz); 7.29-7.36 (3H, m); 7.40-7.48 (2H, m); 7.83-7.91 (2H, m).

Sodium 6-[(5-chloro-2-{[(4-chloro-2-fluorophenyl)methyl]oxy}phenyl)methyl]-2-pyridinecarboxylate Alternative Route 3

Ethyl 6-[(5-chloro-2-{[(4-chloro-2-fluorophenyl)methyl]oxy}phenyl)methyl]-2-pyridinecarboxylate Ethyl 6-[(5-chloro-2-{[(4-chloro-2-fluorophenyl)methyl]oxy}phenyl)methyl]-2-pyridinecarboxylate was prepared using a similar synthetic route to "Alternative route 2".

Sodium 6-[(5-chloro-2-{[(4-chloro-2-fluorophenyl)methyl]oxy}phenyl)methyl]-2-pyridinecarboxylate

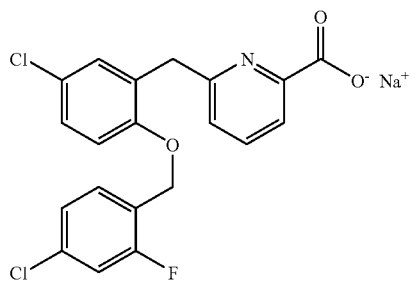

Ethyl 6-[(5-chloro-2-{[(4-chloro-2-fluorophenyl)methyl]oxy}phenyl)methyl]-2-pyridinecarboxylate (204.7 g) was dissolved in ethanol (1.5 L) and stirred under nitrogen at reflux until all the starting material is in solution. 2M Sodium hydroxide (355 ml) was added and the solution heated under reflux for 1 hr 10 minutes. HPLC showed that there was no residual starting material. The solution was filtered and the filter washed with a ~1:1 mixture of hot ethanol (515 ml) and water (520 ml). The combined filtrate and wash were re-heated to reflux, and water (1.5 L) was added slowly over 5 minutes. The solution was then cooled to 20+/−5° C. over 2 hours and stirred for 1 hour. The product was then filtered off and washed with ethanol:water (1:1, 1030 ml), then ethanol:water (~1:3; 385 ml ethanol:1.15 L water). The resulting solid was dried to a constant weight at 60° C. under vacuum, to give the title compound. (186 g).

Sodium 6-[(5-chloro-2-{[(4-chloro-2-fluorophenyl)methyl]oxy}phenyl)methyl]-2-pyridinecarboxylate Alternative Route 4

General Procedure 3

Sodium 6-[(5-chloro-2-{[(4-chloro-2-fluorophenyl)methyl]oxy}phenyl)methyl]-2-pyridinecarboxylate

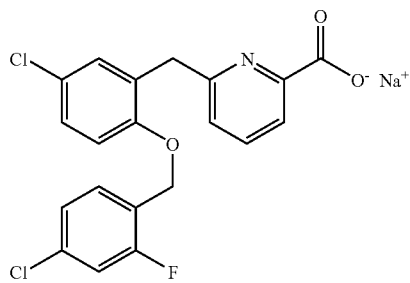

Ethyl 6-[(5-chloro-2-{[(4-chloro-2-fluorophenyl)methyl]oxy}phenyl)methyl]-2-pyridinecarboxylate (108 mg, 0.25 mmol) was dissolved in 3 ml of ethanol and 1 ml of water. Sodium hydroxide (4 equivalents) was added. The mixture was stirred at 60° C. until TLC showed no more SM (starting material) (~2 hours). The reaction mixture was cooled down and extracted with ethyl acetate (3×). Dried over MgSO$_4$. Sodium 6-[(5-chloro-2-{[(4-chloro-2-fluorophenyl)methyl]oxy}-phenyl)methyl]-2-pyridinecarboxylate was obtained as a white solid (94 mg).

Examples 4-26

General Procedure 3A

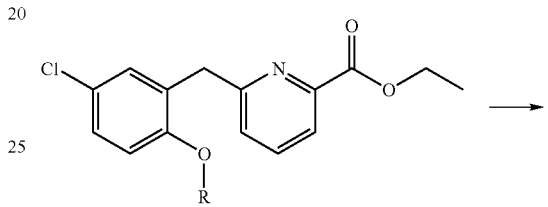

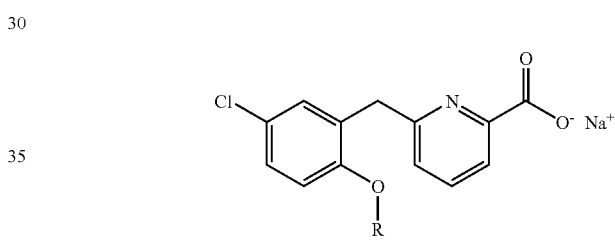

The appropriate ester (~100 mg) was dissolved in 3 ml of EtOH and 1 ml water. Sodium hydroxide (4 equivalents) was added. Heated at 60° C. for two hours. LC/MS showed no more SM (starting material). Cooled down, water added, extracted with ethyl acetate (×3), dried over Magnesium sulfate.

Each of the following Examples (Example 4-Example 26) were prepared from the appropriate ester by a similar method to that described for General Procedure 3 or General Procedure 3A:

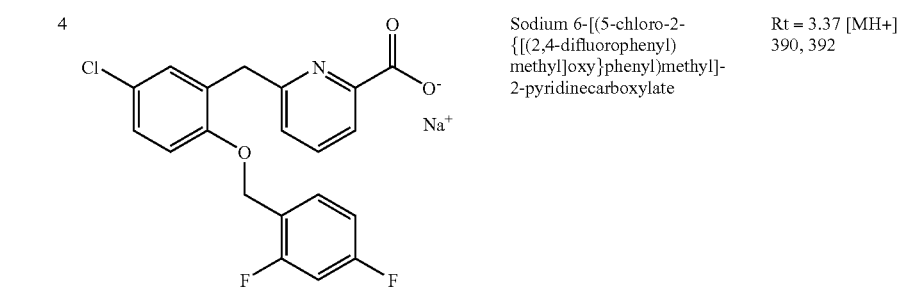

| 4 | | Sodium 6-[(5-chloro-2-{[(2,4-difluorophenyl)methyl]oxy}phenyl)methyl]-2-pyridinecarboxylate | Rt = 3.37 [MH+] 390, 392 |
|---|---|---|---|

-continued

| | | | |
|---|---|---|---|
| 5 | 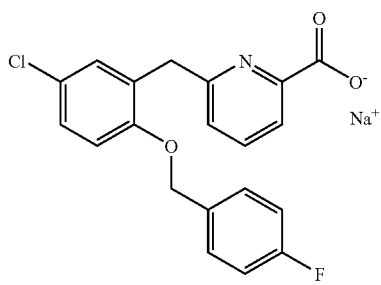 | sodium 6-[(5-chloro-2-{[(4-fluorophenyl)methyl]oxy}phenyl)methyl]-2-pyridinecarboxylate | Rt = 3.25 [MH+] 372, [MH⁻] 370 |
| 6 | 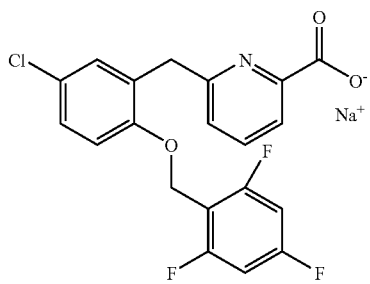 | Sodium 6-[(5-chloro-2-{[(2,4,6-trifluorophenyl)methyl]oxy}phenyl)methyl]-2-pyridinecarboxylate | Rt = 3.34 [MH+] 408, 410, [MH⁻] 406 |
| 7 | 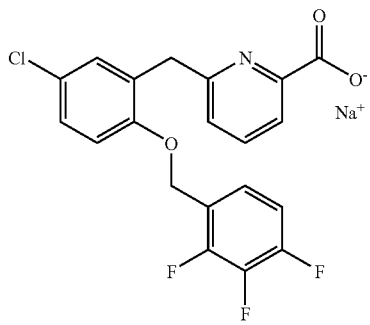 | Sodium 6-[(5-chloro-2-{[(2,3,4-trifluorophenyl)methyl]oxy}phenyl)methyl]-2-pyridinecarboxylate | Rt = 3.41 [MH+] 408, 410, 411 [MH⁻] 406 |
| 8 | 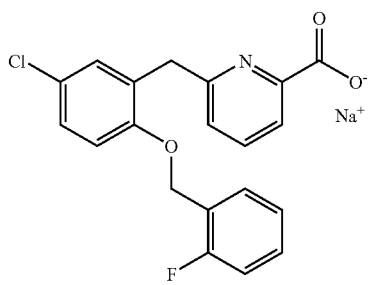 | Sodium 6-[(5-chloro-2-{[(2-fluorophenyl)methyl]oxy}phenyl)methyl]-2-pyridinecarboxylate | Rt = 3.38 [MH+] 372, 374, [MH⁻] 370 |
| 9 | 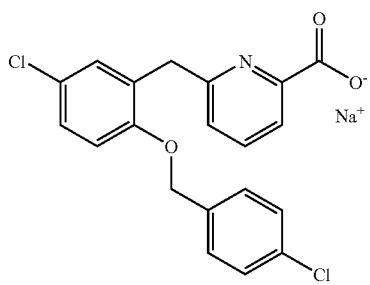 | Sodium 6-[(5-chloro-2-{[(4-chlororophenyl)methyl]oxy}phenyl)methyl]-2-pyridinecarboxylate | Rt = 3.67 [MH+] 388, [MH⁻] 386 |

-continued

| | | | |
|---|---|---|---|
| 10 | 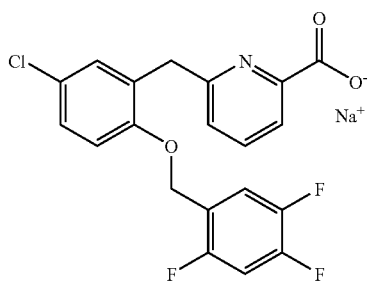 | Sodium 6-[(5-chloro-2-{[(2,4,5-trifluorophenyl)methyl]oxy}phenyl)methyl]-2-pyridinecarboxylate | Rt = 3.4 [MH+] 408, 410 |
| 11 | 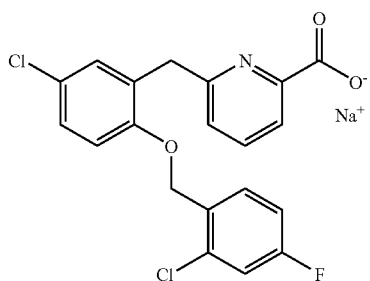 | Sodium 6-[(5-chloro-2-{[(2-chloro-4-fluorophenyl)methyl]oxy}phenyl)methyl]-2-pyridinecarboxylate | Rt = 3.69 [MH+] 406, 409, [MH−] 404 |
| 12 | 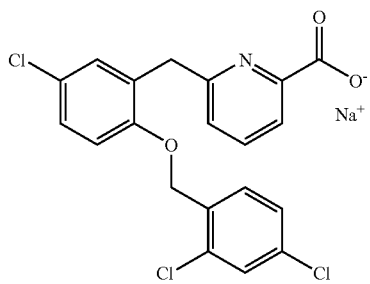 | Sodium 6-[(5-chloro-2-{[(2,4-dichlororophenyl)methyl]oxy}phenyl)methyl]-2-pyridinecarboxylate | Rt = 4.05 [MH+] 424, 426 |
| 13 | 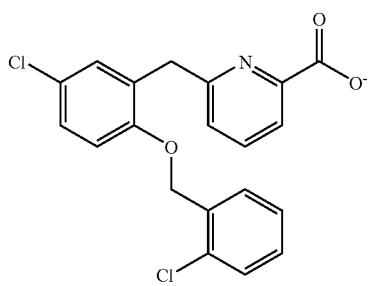 | Sodium 6-[(5-chloro-2-{[(2-chlorophenyl)methyl]oxy}phenyl)methyl]-2-pyridinecarboxylate | Rt = 3.17 [MH+] 387, 390 |
| 14 | 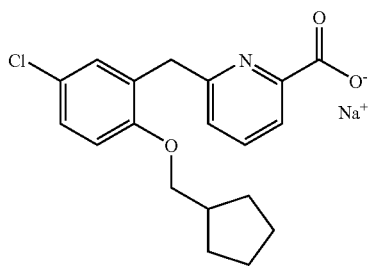 | Sodium 6-({5-chloro-2-[(cyclopentylmethyl)oxy]phenyl}methyl)-2-pyridinecarboxylate | Rt = 3.74 [MH+] 346, 348 |

-continued

| | | | |
|---|---|---|---|
| 15 | 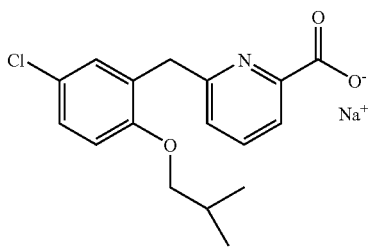 | Sodium 6-({5-chloro-2-[(2-methylpropyl)oxy]phenyl}methyl)-2-pyridinecarboxylate | Rt = 3.44 [MH+] 320, 322, [MH−] 318 |
| 16 | 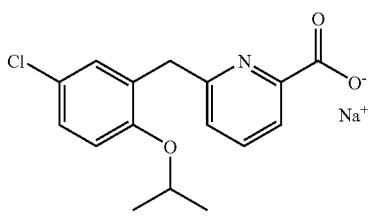 | Sodium 6-({5-chloro-2-[(1-methylethyl)oxy]phenyl}methyl)-2-pyridinecarboxylate | Rt = 2.95 [MH+] 306, 308 |
| 17 | 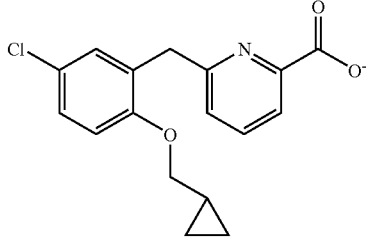 | Sodium 6-({5-chloro-2-[(cyclopropylmethyl)oxy]phenyl}methyl)-2-pyridinecarboxylate | Rt = 2.79 [MH+] 318, 320 |
| 18 | 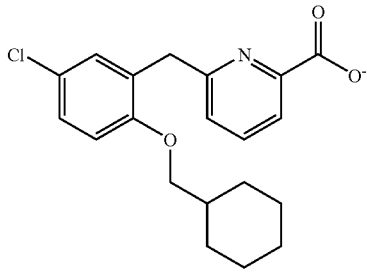 | Sodium 6-({5-chloro-2-[(cyclohexylmethyl)oxy]phenyl}methyl)-2-pyridinecarboxylate | Rt = 3.45 [MH+] 360, 362 |
| 19 | 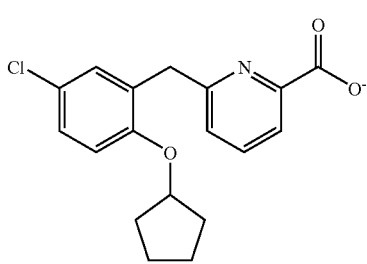 | Sodium 6-{[5-chloro-2-(cyclopentyloxy)phenyl]methyl}-2-pyridinecarboxylate | Rt = 3.02 [MH+] 354, 356 |
| 20 | 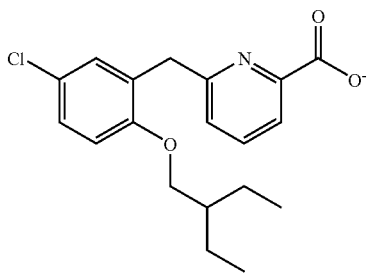 | Sodium 6-({5-chloro-2-[(2-ethylbutyl)oxy]phenyl}methyl)-2-pyridinecarboxylate | Rt = 3.37 [MH+] 348, 350 |

-continued

| | | | |
|---|---|---|---|
| 21 | 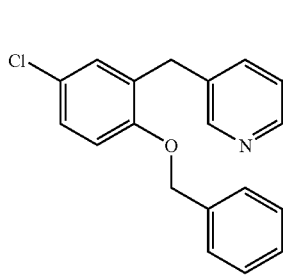 | Sodium 5-({5-chloro-2-[(phenylmethyl)oxy]phenyl}methyl)-3-pyridinecarboxylate | Rt = 3.55 [MH+] 354, 356 |
| 22 | 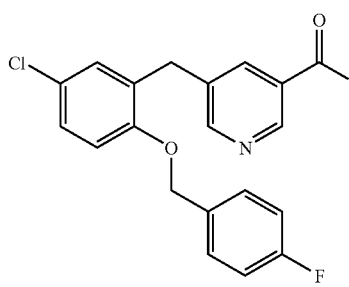 | Sodium 5-[(5-chloro-2-{[(4-fluorophenyl)methyl]oxy}phenyl)methyl]-3-pyridinecarboxylate | Rt = 3.57 [MH+] 372, 374 |
| 23 | 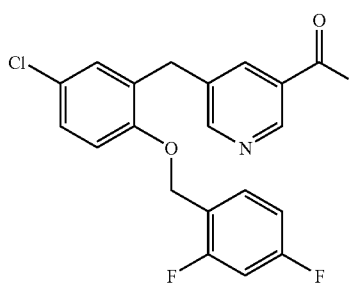 | Sodium 5-[(5-chloro-2-{[(2,4-difluorophenyl)methyl]oxy}phenyl)methyl]-3-pyridinecarboxylate | Rt = 3.58 [MH+] 390, 392 |
| 24 | 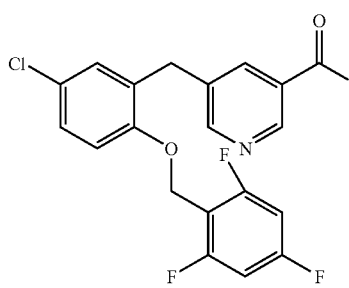 | Sodium 5-[(5-chloro-2-{[(2,4,6-trifluorophenyl)methyl]oxy}phenyl)methyl]-3-pyridinecarboxylate | Rt = 3.50 [MH+] 408, 410 |
| 25 | 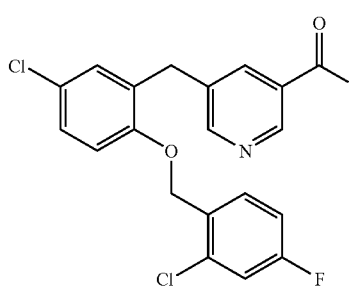 | Sodium 5-[(5-chloro-2-{[(2-chloro-4-fluorophenyl)methyl]oxy}phenyl)methyl]-3-pyridinecarboxylate | Rt = 3.86 [MH+] 406, 409 |

| | | | |
|---|---|---|---|
| 26 | [structure: 5-chloro-2-{[(4-chloro-2-fluorophenyl)methyl]oxy}phenyl)methyl pyridinecarboxylate sodium salt] | Sodium 5-[(5-chloro-2-{[(4-chloro-2-fluorophenyl)methyl]oxy}phenyl)methyl]-3-pyridinecarboxylate | Rt = 3.76 [MH+] 406, 409 |
| 27 | [structure: 5-chloro-2-{[(2,6-difluorophenyl)methyl]oxy}phenyl)methyl pyridinecarboxylate sodium salt] | Sodium 5-[(5-chloro-2-{[(2,6-difluorophenyl)methyl]oxy}phenyl)methyl]-3-pyridinecarboxylate | Rt = 3.49 [MH+] 390, 392 |

Example 28

6-[(5-chloro-2-{[(4-chloro-2-fluorophenyl)methyl]oxy}phenyl)-methyl]-N-(phenylsulphonyl)-2-pyridinecarboxamide

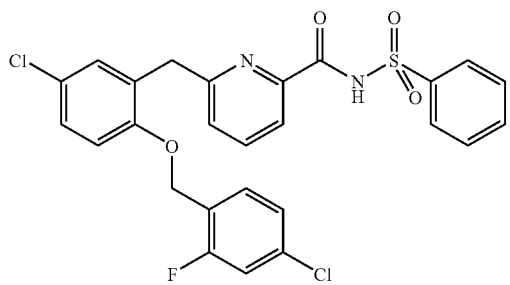

To a solution of 6-[(5-chloro-2-{[(4-chloro-2-fluorophenyl)methyl]oxy}phenyl)-methyl]-2-pyridinecarboxylic acid (81 mg) in dichloromethane (2 ml) and tetrahydrofuran (2 ml) was added benzenesulphonamide (50 mg), 4-dimethyl-aminopyridine (3.5 mg) and N-(3-dimethylaminopropyl)-N'-ethylcarbodiimide hydrochloride (61 mg) and the mixture stirred at ambient temperature for 5 hours. Solvent was removed in vacuo and water (5 ml) added. The mixture was extracted with ether (2×5 ml) and the combined extracts dried (MgSO$_4$) and concentrated in vacuo. The residue was purified by mass-directed autopreparation to afford the title compound (46 mg, 42%) as a white solid. LC/MS [MH+]=545/547, Rt=3.89 min.

Examples 29-36

Examples 29 to 36 were prepared from appropriate intermediates using similar methods to that described in Example 28:

| Ex. | Name | Structure | Rt (min) [MH+] Mol formula |
|---|---|---|---|
| 29 | 6-[(5-Chloro-2-{[(4-chloro-2-fluorophenyl)methyl]oxy}-phenyl)methyl]-N-(methylsulphonyl)-2-pyridinecarboxamide | [structure] | 3.55 min. 483/485 $C_{21}H_{17}Cl_2FN_2O_4S$ |

-continued

| Ex. | Name | Structure | Rt (min) [MH+] Mol formula |
|---|---|---|---|
| 30 | 6-[(5-Chloro-2-{[(4-chloro-2-fluorophenyl)methyl]oxy}-phenyl)methyl]-N-(propylsulphonyl)-2-pyridinecarboxamide | 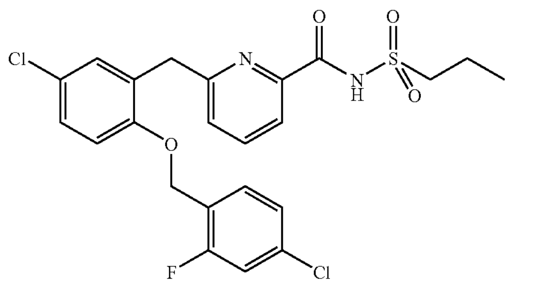 | 3.80 min. 511/513 $C_{23}H_{21}Cl_2FN_2O_4S$ |
| 31 | 6-[(5-Chloro-2-{[(4-chloro-2-fluorophenyl)methyl]oxy}-phenyl)methyl]-N-[(3,5-dichlorophenyl)sulphonyl-2-pyridinecarboxamide | 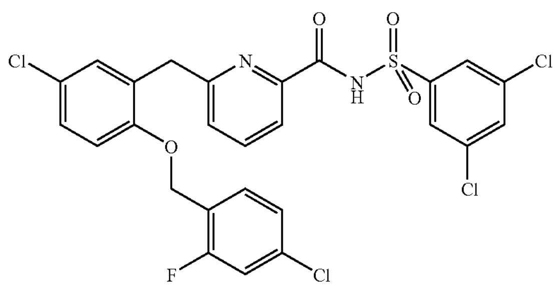 | 4.22 min. 613/615/617 $C_{26}H_{17}Cl_4FN_2O_4S$ |
| 32 | 6-[(5-Chloro-2-{[(4-chloro-2-fluorophenyl)methyl]oxy}-phenyl)methyl]-N-{[4-methoxyphenyl]sulphonyl}-2-pyridine-carboxamide | 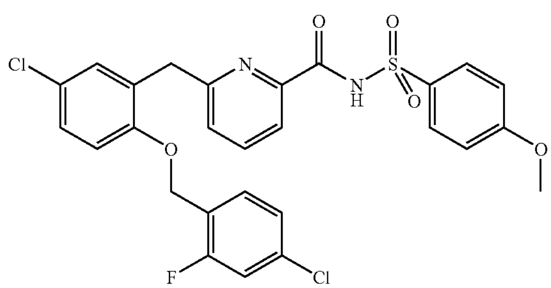 | 3.93 min. 575/577 $C_{27}H_{21}Cl_2FN_2O_5S$ |
| 33 | N-[(4-Bromophenyl)sulphonyl]-6-[(5-chloro-2-{[(4-chloro-2-fluorophenyl)methyl]oxy}phenyl)-methyl]-2-pyridinecarboxamide | 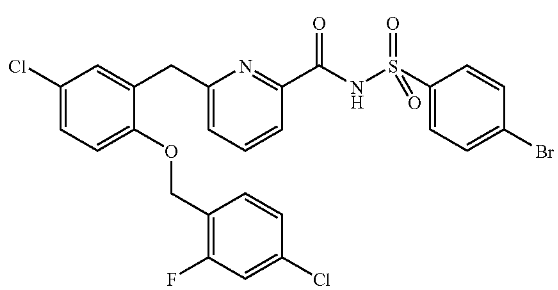 | 4.11 min. 623/625/627 $C_{26}H_{18}BrCl_2FN_2O_4S$ |
| 34 | N-[(3-Bromophenyl)sulphonyl]-6-[(5-chloro-2-{[(4-chloro-2-fluorophenyl)methyl]oxy}phenyl)-methyl]-2-pyridinecarboxamide | 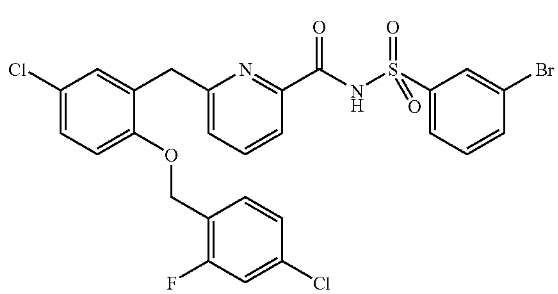 | 4.11 min. 623/625/627 $C_{26}H_{18}BrCl_2FN_2O_4S$ |

-continued

| Ex. | Name | Structure | Rt (min) [MH+] Mol formula |
|---|---|---|---|
| 35 | N-{[4-(Acetylamino)phenyl]-sulphonyl}-6-[(5-chloro-2-{[(4-chloro-2-fluorophenyl)methyl]-oxy}phenyl)methyl]-2-pyridine-carboxamide | 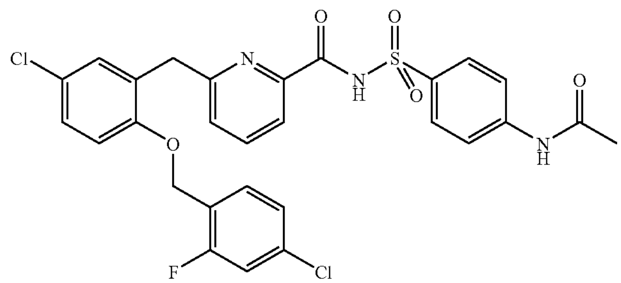 | 3.63 min. 602/604 $C_{28}H_{22}Cl_2FN_3O_5S$ |
| 36 | 6-[(5-Chloro-2-{[(4-chloro-2-fluorophenyl)methyl]oxy}-phenyl)methyl]-N-[(3,5-dimethyl-4-isoxazolyl)sulphonyl]-2-pyridinecarboxamide | 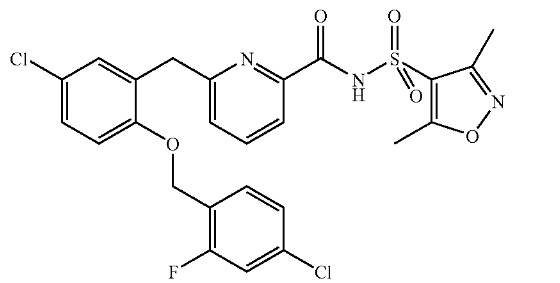 | 3.91 min. 564/566 $C_{25}H_{20}Cl_2FN_3O_5S$ |

Example 37

4-Chloro-6-[(5-chloro-2-{[(4-chloro-2-fluorophenyl)-methyl]oxy}phenyl)methyl]-2-pyridinecarboxylic acid, sodium salt

Methyl 4-chloro-6-(chloromethyl)-2-pyridinecarboxylate

To a solution of methyl 4-chloro-6-(hydroxymethyl)-2-pyridinecarboxylate (166 mg, Ref: Kittika et al., *Tetrahedron*, 44 (10), 2821, (1988)) in dry dichloromethane (3 ml) was added thionyl chloride (66 µl). The solution was stirred for 40 minutes. LC/MS indication reaction completion. Solvent was removed u.r.p. (under reduced pressure) to give a white solid. Toluene (~2 ml) added then removed u.r.p. The residue was dried in vacuo to give a white solid. (175 mg, 97%). LC/MS [MH+]=220/222, Rt=2.51 min. Title compound obtained as the free base.

Methyl 4-chloro-6-[(5-chloro-2-{[(4-chloro-2-fluorophenyl)methyl]-oxy}phenyl)methyl]-2-Pyridinecarboxylate To a stirring solution of methyl 4-chloro-6-(chloromethyl)-2-pyridinecarboxylate (175 mg), in dry toluene (4 ml) and ethanol (4 ml) was added (5-chloro-2-{[(4-chloro-2-fluorophenyl)methyl]oxy}phenyl)boronic acid (250 mg), potassium carbonate (330 mg) and tetrakis(triphenylphosphine)-palladium(0) (92 mg). The mixture was stirred under reflux for 2 hours. Solvent was removed u.r.p. (under reduced pressure) and water (20 ml) and ether (20 ml) added to the residue. Insoluble solid was filtered off over Hyflo and washed with ether. The aqueous layer was separated off and washed with ether (15 ml), and the combined ether layers washed with brine (10 ml), dried over MgSO₄ and evaporated down u.r.p. The residue was purified by mass-directed autopreparation to give a white solid (46.3 mg, 12.8%). LC/MS [MH+]=468/470/472, Rt=4.11 min. NMR and LC/MS indicated that transesterification had occurred to give the ethyl ester.

4-Chloro-6-[(5-chloro-2-{[(4-chloro-2-fluorophenyl)-methyl]oxy}phenyl)methyl]-2-pyridinecarboxylic acid, sdium salt

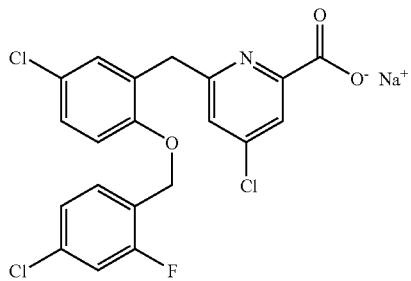

Methyl 4-chloro-6-[(5-chloro-2-{[(4-chloro-2-fluorophenyl)methyl]-oxy}phenyl)methyl]-2-pyridinecarboxylate (46.3 mg), 2N sodium hydroxide (0.25 ml) and ethanol (1 ml) were stirred at room temperature for 1 hour. LC/MS indicated reaction completion. Solvent was removed u.r.p (under reduced pressure) and water (~5 ml) added to the residue. The mixture was extracted with ethyl acetate (2×5 ml) and the combined extracts washed with brine (4 ml), dried over MgSO₄ and evaporated down u.r.p. The residue was washed with hexane and dried in vacuo at 50° C. to afford the title compound (35.6 mg, 77.9%) as a pale pink solid. LC/MS [MH+]=440/442/444, Rt=3.57 min.

Example 38

2-[(5-Chloro-2-{[(4-chloro-2-fluorophenyl)methyl]oxy}phenyl)-methyl]-6-(1H-tetrazol-5-yl)pyridine 6-[(5-Chloro-2-{[(4-chloro-2-fluorophenyl)methyl]oxy}phenyl)methyl]-2-pyridinecarboxamide 6-[(5-Chloro-2-{[(4-chloro-2-fluorophenyl)methyl]oxy}phenyl)-methyl]-2-pyridinecarboxylic acid (300 mg) was suspended in DCM (1.5 ml). Thionyl chloride (268 µl) was added and the mixture heated to reflux for 2 hours. Upon cooling to room temperature, the mixture was evaporated. The residue was dissolved in THF (2.95 mL) and a 0.88 ammonia solution (1.5 mL) was added. After 1 hour the mixture was evaporated to give a cream-coloured solid which was partitioned between EtOAc and saturated aqueous sodium bicarbonate. The layers were separated and the EtOAc layer was dried ($Na_2SO_4$), filtered and concentrated. The residue was purified by chromatography on silica gel with hexane containing EtOAc (30-50%) to afford the title compound (223 mg, 74%).

LC/MS [ES+]=405/407, RT=3.42 min.

6-[(5-Chloro-2-{[(4-chloro-2-fluorophenyl)methyl]oxy}phenyl)methyl]-2-pyridinecarbonitrile A solution of 6-[(5-chloro-2-{[(4-chloro-2-fluorophenyl)methyl]oxy}phenyl)-methyl]-2-pyridinecarboxamide (115 mg) in phosphoryl chloride (1.25 ml) was stirred at 60° C. for 5 hours. Excess phosphoryl chloride was removed in vacuo and ethyl acetate (5 ml) added. The solution was washed with saturated sodium bicarbonate solution (5 ml), and the aqueous layer extracted with ethyl acetate (5 ml). The combined extracts were washed with brine (5 ml), dried ($MgSO_4$) and concentrated in vacuo. The residue was purified by mass-directed autopreparation to afford the title compound (93 mg, 85%) as a white solid.

LC/MS [MH−]=387/389, RT=3.77 min.

2-[(5-Chloro-2-{[(4-chloro-2-fluorophenyl)methyl]oxy}phenyl)-methyl]-6-(1H-tetrazol-5-yl)pyridine

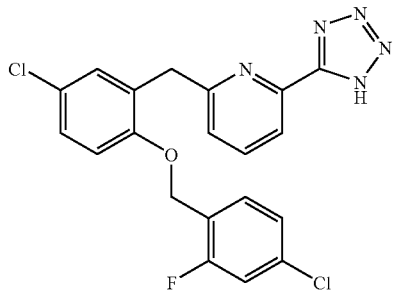

A mixture of 6-[(5-chloro-2-{[(4-chloro-2-fluorophenyl)methyl]oxy}phenyl)-methyl]-2-pyridinecarbonitrile (93 mg), sodium azide (51 mg), ammonium chloride (42 mg) and dimethylformamide (1 ml) was stirred at 120° for 11 hours. After cooling, water (5 ml) was added and the mixture extracted with ethyl acetate (2×5 ml). The combined extracts were dried ($MgSO_4$) and concentrated in vacuo. The residue was purified by mass-directed autopreparation to afford the title compound (29.7 mg, 29%) as a white solid.

LC/MS [MH+]=430/432, RT=3.38 min.

Example 39

6-[(5-Chloro-2-{[(4-chloro-2-fluorophenyl)methyl]oxy}-phenyl)methyl]-5-methyl-2-pyridinecarboxylic acid, sodium salt 5,6-Dimethyl-2-pyridinecarbonitrile 1-oxide To a solution of 5,6-dimethyl-2-pyridinecarbonitrile (3.68 g, Ref: Guay et al., *Bioorg. Med. Chem. Letters*, 8 (5), 453, (1998)) in chloroform (25 ml) was added dropwise a solution of m-chloroperbenzoic acid (7.35 g) in chloroform (75 ml) and the solution stirred at ambient temperature for 40 hours. Sodium sulphite (2.4 g) was added and the mixture stirred for 1 hour, filtered and the solid washed with dichloromethane. The filtrate was washed with saturated sodium bicarbonate (50 ml) and water (50 ml), dried ($MgSO_4$) and concentrated in vacuo. The residue was recrystallised from ether to afford the title compound (3.44 g, 83%) as a white solid. LC/MS [MH+]=149, RT=1.30 min.

(6-Cyano-3-methyl-2-pyridinyl)methyl acetate

To acetic anhydride (12 ml) at 120° C. was added 5,6-dimethyl-2-pyridine-carbonitrile 1-oxide (3.02 g) and the solution heated at 120° C. for 5 minutes then under reflux for 2.5 hours. After cooling the solution was added to ice (ca. 80 g) and the mixture neutralized with sodium bicarbonate. It was extracted with ether (80 ml then 2×40 ml) and the combined extracts washed with brine (40 ml), dried ($MgSO_4$) and concentrated in vacuo. The residue was purified by Biotage chromatography eluting with 2:1 hexane:ethyl acetate to afford the title compound (2.60 g, 67%) as a pale yellow solid. LC/MS [MH+]=191, RT=2.05 min.

6-(Hydroxymethyl)-5-methyl-2-pyridinecarbonitrile

Potassium carbonate (65 mg) was added to a solution of (6-cyano-3-methyl-2-pyridinyl)methyl acetate (2.89 g) in methanol (20 ml) and the mixture stirred under argon at ambient temperature for 2.5 hours. It was concentrated in vacuo to ca. ½ volume and water (40 ml) added. The mixture was neutralized with 5% acetic acid (1.2 ml) and extracted with dichloromethane (40 ml then 2×20 ml). The combined extracts were washed with brine (20 ml), dried ($MgSO_4$) and concentrated in vacuo. The residue was purified by Biotage chromatography eluting with 2:1 hexane:ethyl acetate to afford the title compound (1.45 g, 64%) as a pale buff solid. LC/MS [MH+]=149, RT=1.46 min.

6-(Chloromethyl)-5-methyl-2-pyridinecarbonitrile

A solution of 6-(hydroxymethyl)-5-methyl-2-pyridinecarbonitrile (184 mg) and thionyl chloride (0.16 ml) in dichloromethane (3.5 ml) was stirred at ambient temperature for 7 hours. Solvent was removed in vacuo and toluene (2 ml) added then removed in vacuo to afford the title compound (205 mg, 99%) as a pale buff solid.

LC/MS [MH+]=167/169, RT=2.44 min.

6-[(5-chloro-2-{[(4-chloro-2-fluorophenyl)methyl]oxy}phenyl)methyl]-5-methyl-2-pyridinecarbonitrile To a solution of 6-(chloromethyl)-5-methyl-2-pyridinecarbonitrile (132.5 mg) in dry toluene (4 ml) and ethanol (4 ml)

was added (5-chloro-2-{[(4-chloro-2-fluorophenyl)methyl]oxy}phenyl)boronic acid (250 mg), potassium carbonate (330 mg) and tetrakis(triphenylphosphine)palladium(0) (92 mg) and the mixture stirred under reflux for 2 hours. Solvent was removed in vacuo and water (20 ml) and ether (20 ml) added. Insoluble solid was filtered over Celite and washed with ether. The aqueous layer was further extracted with ether (15 ml) and the combined extracts washed with brine (10 ml), dried (MgSO$_4$) and concentrated in vacuo. The residue was purified by mass-directed autopreparation to afford the title compound (129 mg, 40%) as a pale buff solid.

LC/MS [MH+]=401/403, RT=3.87 min.

6-[(5-Chloro-2-{[(4-chloro-2-fluorophenyl)methyl]oxy}phenyl)methyl]-5-methyl-2-pyridinecarboxamide A solution of 6-[(5-chloro-2-{[(4-chloro-2-fluorophenyl)methyl]oxy}phenyl)-methyl]-5-methyl-2-pyridinecarbonitrile (127 mg) in 2M sodium hydroxide solution (0.8 ml) and ethanol (4 ml) was stirred under reflux for 2 hours. Solvent was removed in vacuo and water (5 ml) added. The mixture was extracted with ethyl acetate (3×5 ml) and the combined extracts washed with brine (5 ml), dried (MgSO$_4$) and concentrated in vacuo to afford the title compound (107 mg, 81%) as a white solid. LC/MS [MH+]=419/421, RT=3.57 min.

6-[(5-Chloro-2-{[(4-chloro-2-fluorophenyl)methyl]oxy}phenyl)methyl]-5-methyl-2-pyridinecarboxylic acid, sodium salt

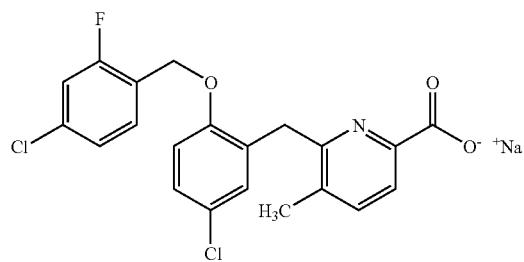

A solution of 6-[(5-Chloro-2-{[(4-chloro-2-fluorophenyl)methyl]oxy}phenyl)-methyl]-5-methyl-2-pyridinecarboxamide (105 mg) in conc. hydrochloric acid (6 ml) and dioxan (6 ml) was stirred under reflux for 4 hours. Solvent was removed in vacuo and the residue was purified by mass-directed auto-preparation. It was dissolved in ethanol (4 ml) and 2M sodium hydroxide solution (0.3 ml) added. Solvent was removed in vacuo and water (5 ml) added. The mixture was extracted with ethyl acetate (3×5 ml) and the combined extracts washed with brine (5 ml), dried (MgSO$_4$) and concentrated in vacuo to afford the title compound (36 mg, 33%) as a white solid. LC/MS [MH+]=420/422, RT=3.19 min.

Example 40

6-[(5-Chloro-2-{[(4-chloro-2-fluorophenyl)methyl]oxy}-phenyl)methyl]-3-methyl-2-pyridinecarboxylic acid, sodium salt

(a). 3,6-Dimethyl-2-pyridinecarbonitrile 1-oxide

To a solution of 3,6-dimethyl-2-pyridinecarbonitrile (8.20 g, may be prepared as described in Russell et al., J. Med. Chem., 48(5), 1367, (2005)) in chloroform (60 ml) was added dropwise a solution of m-chloroperbenzoic acid (20 g) in chloroform (210 ml) and the solution stirred at ambient temperature for 7 hours. Sodium sulphite (2.4 g) was added and the mixture stirred for 1.5 hours, filtered and the solid washed with dichloromethane. The filtrate was washed with saturated sodium bicarbonate (120 ml) and water (120 ml), dried (MgSO$_4$) and concentrated in vacuo. The residue was recrystallised from ether to afford the title compound (5.28 g, 58%) as a pale yellow solid.

LC/MS [MH+]=149, RT=1.31 min.

(b). (6-Cyano-5-methyl-2-pyridinyl)methyl acetate

To acetic anhydride (20 ml) at 120° was added 3,6-dimethyl-2-pyridine-carbonitrile 1-oxide (5.28 g) and the solution heated at 120° for 5 minutes then under reflux for 2 hours. After cooling the solution was added to ice (ca. 150 g) and the mixture neutralized with sodium bicarbonate. It was extracted with ether (170 ml then 2×75 ml) and the combined extracts washed with brine (60 ml), dried (MgSO$_4$) and concentrated in vacuo. The residue was purified by Biotage chromatography eluting with 2:1 hexane:ethyl acetate to afford the title compound (3.62 g, 67%) as a pale yellow oil LC/MS [MH+]=191, RT=2.16 min.

(c). 6-(Hydroxymethyl)-3-methyl-2-pyridinecarbonitrile

Potassium carbonate (82 mg) was added to a solution of (6-cyano-5-methyl-2-pyridinyl)methyl acetate (3.62 g) in methanol (25 ml) and the mixture stirred under argon at ambient temperature for 2 hours. It was concentrated in vacuo to ca. ¼ volume and water (50 ml) added. The mixture was neutralized with 5% acetic acid (1.5 ml) and extracted with dichloromethane (50 ml then 2×25 ml). The combined extracts were washed with brine (25 ml), dried (MgSO$_4$) and concentrated in vacuo. The residue was recrystallised from ether:hexane to afford the title compound (2.26 g, 80%) as a pale buff solid.

LC/MS [MH+]=149, RT=1.50 min.

(d). 6-(Chloromethyl)-3-methyl-2-pyridinecarbonitrile

A solution of 6-(Hydroxymethyl)-3-methyl-2-pyridinecarbonitrile (148 mg) and thionyl chloride (0.16 ml) in dichloromethane (3.5 ml) was stirred at ambient temperature for 6 hours. Solvent was removed in vacuo and toluene (2 ml) added then removed in vacuo to afford the title compound (160 mg, 96%) as a pale grey-green solid.

LC/MS [MH+]=167/169, RT=2.40 min.

(e). 6-[(5-chloro-2-{[(4-chloro-2-fluorophenyl)methyl]oxy}phenyl)methyl]-3-methyl-2-pyridinecarbonitrile To a solution of 6-(Chloromethyl)-3-methyl-2-pyridinecarbonitrile (132.5 mg) in dry toluene (4 ml) and ethanol (4 ml) was added (5-chloro-2-{[(4-chloro-2-fluorophenyl)methyl]oxy}phenyl)boronic acid (250 mg), potassium carbonate (330 mg) and tetrakis(triphenylphosphine)palladium(0) (92 mg) and the mixture stirred under reflux for 2.5 hours. Solvent was removed in vacuo and water (20 ml) and ether (20 ml) added. Insoluble solid was filtered over Celite and washed with ether. The aqueous layer was further extracted with ether (15 ml) and the combined extracts washed with brine (10 ml), dried (MgSO$_4$) and concentrated in vacuo. The residue was purified by mass-directed autopreparation to afford the title compound (204 mg, 64%) as a white solid.

LC/MS [MH+]=401/403, RT=3.85 min.

(f). 6-[(5-Chloro-2-{[(4-chloro-2-fluorophenyl)methyl]oxy}phenyl)methyl]-3-methyl-2-pyridinecarboxylic acid, sodium salt

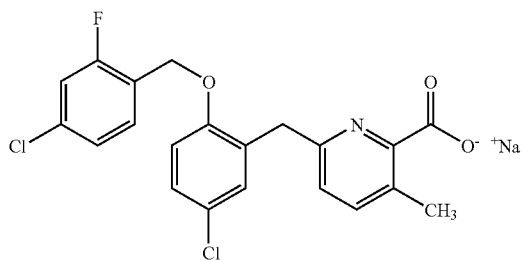

A solution of 6-[(5-chloro-2-{[(4-chloro-2-fluorophenyl)methyl]oxy}phenyl)-methyl]-3-methyl-2-pyridinecarbonitrile (202 mg) in 20% sodium hydroxide solution (3 ml) and ethanol (2 ml) was stirred under reflux for 12 hours. Solvent was removed in vacuo and the residue washed with water and ether and dried in vacuo at 40° to afford the title compound (60 mg, 27%) as a white solid.

LC/MS [MH+]=420/422, RT=3.52 min.

Example 41

6-({5-Chloro-2-[(1,1-dimethylethyl)oxy]phenyl}methyl)-2-pyridinecarboxylic acid (a). 6-[(5-chloro-2-hydroxyphenyl)methyl]-2-pyridinecarboxylic acid A mixture of ethyl 6-[(5-chloro-2-{[(4-chloro-2-fluorophenyl)methyl]oxy}-phenyl)methyl]-2-pyridinecarboxylate (453 mg), sodium thiomethoxide (370 mg) and dimethylformamide (5 ml) was stirred at 100° C. for 2.5 hours. After cooling water (30 ml) was added and the mixture extracted with ethyl acetate (2×25 ml). The aqueous layer was acidified with conc. hydrochloric acid and extracted with ethyl acetate (2×25 ml). The combined extracts were washed with water (10 ml), dried (MgSO$_4$) and concentrated in vacuo. The residue was washed with water and recrystallised from ether to afford the title compound (208 mg, 76%) as a pale buff solid.

LC/MS [MH+]=264/266, RT=2.04 min.

(b). 6-({5-Chloro-2-[(1,1-dimethylethyl)oxy]phenyl}methyl)-2-pyridine-carboxylic acid

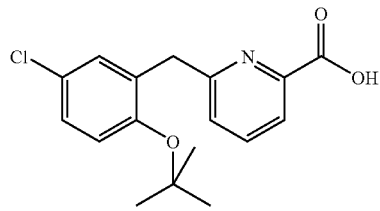

To a solution/suspension of 6-[(5-chloro-2-hydroxyphenyl)methyl]-2-pyridine-carboxylic acid (308 mg) in dry dichloromethane (12 ml) was added t-butyl 2,2,2-trichloroacetimidate (1.67 ml) and boron trifluoride-diethyl etherate (0.05 ml) and the mixture stirred under argon at ambient temperature for 44 hours. Dichloromethane (15 ml) was added and the mixture washed with saturated sodium bicarbonate solution (15 ml). The aqueous layer was extracted with dichloromethane (2×15 ml) and the combined organic extracts washed with brine (25 ml), dried (MgSO$_4$) and concentrated in vacuo. The residue was purified by mass-directed autopreparation to afford the title compound (91 mg, 24%) as a white solid.

LC/MS [MH−]=318/320, RT=3.58 min

It is to be understood that the present invention covers all combinations of particular and preferred subgroups described herein above.

Assays for Determining Biological Activity

The compounds of formula (I) can be tested using the following assays to demonstrate their prostanoid antagonist or agonist activity in vitro and in vivo and their selectivity. Prostaglandin receptors that may be investigated are DP, EP$_1$, EP$_2$, EP$_3$, EP$_4$, FP, IP and TP.

Biological Activity at EP$_1$ and EP$_3$ Receptors

The ability of compounds to antagonise EP$_1$ & EP$_3$ receptors may be demonstrated using a functional calcium mobilisation assay. Briefly, the antagonist properties of compounds are assessed by their ability to inhibit the mobilisation of intracellular calcium ([Ca$^{2+}$]$_i$) in response to activation of EP$_1$ or EP$_3$ receptors by the natural agonist hormone prostaglandin E$_2$ (PGE$_2$). Increasing concentrations of antagonist reduce the amount of calcium that a given concentration of PGE$_2$ can mobilise. The net effect is to displace the PGE$_2$ concentration-effect curve to higher concentrations of PGE$_2$. The amount of calcium produced is assessed using a calcium-sensitive fluorescent dye such as Fluo-4, AM and a suitable instrument such as a Fluorimetric Imaging Plate Reader (FLIPR). Increasing amounts of [Ca$^{2+}$]$_i$ produced by receptor activation increase the amount of fluorescence produced by the dye and give rise to an increasing signal. The signal may be detected using the FLIPR instrument and the data generated may be analysed with suitable curve-fitting software.

The human EP$_1$ or EP$_3$ calcium mobilisation assay (hereafter referred to as 'the calcium assay') utilises Chinese hamster ovary-K1 (CHO-K1) cells into which a stable (pCIN; BioTechniques 20 (1996): 102-110) vector containing either EP$_1$ or EP$_3$ cDNA has previously been transfected. Cells are cultured in suitable flasks containing culture medium such as DMEM:F-12 supplemented with 10% v/v foetal calf serum, 2 mM L-glutamine, 0.25 mg/ml geneticin, 100 μM flurbiprofen and 10 g/ml puromycin.

For assay, cells are harvested using a proprietary reagent that dislodges cells such as Versene. Cells are re-suspended in a suitable quantity of fresh culture media for introduction into a 384-well plate. Following incubation for 24 hours at 37° C. the culture media is replaced with a medium containing Fluo-4 and the detergent pluronic acid, and a further incubation takes place. Concentrations of compounds are then added to the plate in order to construct concentration-effect curves. This may be performed on the FLIPR in order to assess the agonist properties of the compounds. Concentrations of PGE$_2$ are then added to the plate in order to assess the antagonist properties of the compounds.

The data so generated may be analysed by means of a computerised curve-fitting routine. The concentration of compound that elicits a half-maximal inhibition of the calcium mobilisation induced by $PGE_2$ ($pIC_{50}$) may then be estimated.

Binding Assay for the Human Prostanoid $EP_1$ Receptor

Competition assay using $[^3H]$-PGE2.

Compound potencies are determined using a radioligand binding assay. In this assay compound potencies are determined from their ability to compete with tritiated prostaglandin $E_2$ ($[^3H]$-$PGE_2$) for binding to the human $EP_1$ receptor.

This assay utilises Chinese hamster ovary-K1 (CHO-K1) cells into which a stable vector containing the $EP_1$ cDNA has previously been transfected. Cells are cultured in suitable flasks containing culture medium such as DMEM:F-12 supplemented with 10% v/v foetal calf serum, 2 mM L-glutamine, 0.25 mg/ml geneticin, 10 µg/ml puromycin and 10 µM indomethacin.

Cells are detached from the culture flasks by incubation in calcium and magnesium free phosphate buffered saline containing 1 mM disodium ethylenediaminetetraacetic acid ($Na_2EDTA$) and 10 µM indomethacin for 5 min. The cells are isolated by centrifugation at 250×g for 5 mins and suspended in an ice cold buffer such as 50 mM Tris, 1 mM $Na_2EDTA$, 140 mM NaCl, 10 µM indomethacin (pH 7.4). The cells are homogenised using a Polytron tissue disrupter (2×10s burst at full setting), centrifuged at 48,000×g for 20 mins and the pellet containing the membrane fraction is washed (optional) three times by suspension and centrifugation at 48,000×g for 20 mins. The final membrane pellet is suspended in an assay buffer such as 10 mM 2-[N-morpholino]ethanesulphonic acid, 1 mM $Na_2EDTA$, 10 mM $MgCl_2$ (pH 6). Aliquots are frozen at −80° C. until required.

For the binding assay the cell membranes, competing compounds and $[^3H]$-$PGE_2$ (3 nM final assay concentration) are incubated in a final volume of 100 µl for 30 min at 30° C. All reagents are prepared in assay buffer. Reactions are terminated by rapid vacuum filtration over GF/B filters using a Brandell cell harvester. The filters are washed with ice cold assay buffer, dried and the radioactivity retained on the filters is measured by liquid scintillation counting in Packard TopCount scintillation counter.

The data are analysed using non linear curve fitting techniques to determine the concentration of compound producing 50% inhibition of specific binding ($IC_{50}$).

Biological Activity at TP Receptor

To determine if a compound has agonist or antagonist activity at the TP receptor a functional calcium mobilisation assay may be performed. Briefly, the antagonist properties of compounds are assessed by their ability to inhibit the mobilisation of intracellular calcium ($[Ca^{2+}]_i$) in response to activation of TP receptors by the stable $TXA_2$ mimetic U46619 (9,11-dideoxy-11α,9α-epoxy-methanoprostaglandin F2 α; commercially available from e.g Sigma-Aldrich). Increasing concentrations of antagonist reduce the amount of calcium that a given concentration of U46619 can mobilise. The net effect is to displace the U46619 concentration-effect curve. The amount of calcium produced is assessed using a calcium-sensitive fluorescent dye such as Fluo-4, AM and a suitable instrument such as a Fluorimetric Imaging Plate Reader (FLIPR). Increasing amounts of $[Ca^{2+}]_i$ produced by receptor activation increase the amount of fluorescence produced by the dye and give rise to an increasing signal. The signal may be detected using the FLIPR instrument and the data generated may be analysed with suitable curve-fitting software.

The agonist activity of the compounds are determined by their ability to cause an increase in intracellular mobilisation in the absence of U46619.

The human TP calcium mobilisation assay utilises Chinese hamster ovary-K1 (CHO-K1) cells into which a stable (pCIN; BioTechniques 20 (1996): 102-110) vector containing TP cDNA has previously been transfected. Cells are cultured in suitable flasks containing culture medium such as DMEM:F-12 supplemented with 10% v/v foetal calf serum, 2 mM L-glutamine, 0.25 mg/ml geneticin, 100 µM flurbiprofen and 10 µg/ml puromycin.

For assay, cells are harvested using a proprietary reagent that dislodges cells such as Versene. Cells are re-suspended in a suitable quantity of fresh culture media for introduction into a 96-well plate. Following incubation for 24 hours at 37° C. the culture media is replaced with a medium containing Fluo-4 and the detergent pluronic acid, and a further incubation takes place. Concentrations of compounds are then added to the plate in order to construct concentration-effect curves. This may be performed on the FLIPR in order to assess the agonist properties of the compounds. Concentrations of U46619 are then added to the plate in order to assess the antagonist properties of the compounds.

The data so generated may be analysed by means of a computerised curve-fitting routine. The concentration of compound that elicits a half-maximal inhibition of the calcium mobilisation induced by U46619 ($pIC_{50}$) may then be estimated, and the percentage activation caused by the compounds directly can be used to determine if there is any agonism present.

Results

Where results are presented in respect of the compound of Example 3, they refer to the sodium salt.

The compounds of examples 1-41 were tested in the binding assay for the human prostanoid $EP_1$ receptor. The results are expressed as $pIC_{50}$ values. A $pIC_{50}$ is the negative logarithms of the $IC_{50}$. The results given are averages of a number of experiments. The compounds of examples 1-26 and 28-41 had a $pIC_{50}$ value $\geq 6$. More particularly, the compounds of examples 3, 4, 10-12, 14, 28-30, 33-34, 36 and 38-39 exhibited a $pIC_{50}$ value $\geq 7.5$. The compounds of examples 27 and 41 exhibited $pIC_{50}$ values of <6.

The compounds of examples 2-20 and 28-41 (free bases or sodium salts) were tested in the human $EP_1$ calcium mobilisation assay. The results are expressed as functional $pK_i$ values. A functional $pK_i$ is the negative logarithms of the antagonist dissociation constant as determined in the human $EP_1$ calcium mobilisation assay. The results given are averages of a number of experiments. The compounds of examples 2-20, 28-30 and 33-39 exhibited a functional $pK_i$ value >6. More particularly, the compounds of examples 2-4 12, 13, 18 28-30, 34 and 36-38 exhibited a functional $pK_i$ value of $\geq 7.5$. The compounds of examples 31-32 and 40-41 exhibited a functional $pK_i$ value <6.

The compounds of examples 2-4, 8-20 and 28-41 (free bases or sodium salts) were tested in the human $EP_3$ calcium mobilisation assay. The results are expressed as functional $pK_i$ values. A functional $pK_i$ is the negative logarithms of the antagonist dissociation constant as determined in the human $EP_3$ calcium mobilisation assay. The results given are averages of a number of experiments. The compounds of examples 2-4, 8-20 and 28-41 exhibited a functional pKi value of $\leq 6.5$. The compounds of examples 2, 4, 8-11, 15-17, 19, 28-32, 35-36 and 40 exhibit a functional pKi value of <5.

The compounds of examples 1, 3-15, 28-30, 33-34, 36 and 38-39 (free bases or sodium salts) were tested in the human TP calcium mobilisation assay. The results are expressed as functional $pK_i$ values. A functional pKi is the negative logarithms of the antagonist dissociation constant as determined in the human TP calcium mobilisation assay. The compounds of examples 3-12, 14, 28, 30, 34, 36, 38 and 39 exhibited a functional pKi of >6. More particularly, the compounds of examples 3, 12, 34, 38 and 39 exhibited a functional pKi of ≧7.5. The compounds of examples 1, 13, 15, 29 and 33 exhibited a functional pKi of <6.

No toxicological effects were observed in these tests.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation the following claims:

The invention claimed is:

1. A compound of formula (IA) comprising

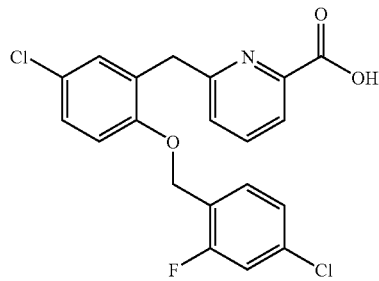

and a pharmaceutically acceptable salt thereof.

2. The compound of claim 1 wherein the compound is the sodium salt.

3. The compound of claim 1 wherein the compound is the tris(hydroxymethyl)aminomethane salt.

4. A pharmaceutical composition comprising a compound according to claim 1 or a pharmaceutically acceptable salt thereof together with one or more physiologically acceptable carriers or excipients.

5. A process for preparing a compound of formula (IA) according to claim 4 comprising:

reacting a compound of formula (II):

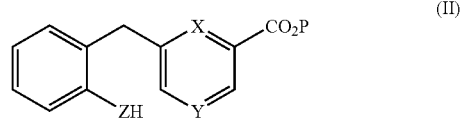

wherein P is a protecting group and Z is O, X is N, and Y is CH, with a compound $R^x$-L; wherein $R^x$ is as defined as

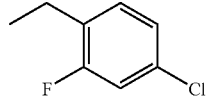

and L is Cl, Br or OH.

6. The process of claim 5, further comprising the step or steps of, in any order, effecting deprotection;

forming a pharmaceutically acceptable salt thereof.

* * * * *